United States Patent
Panicker et al.

(10) Patent No.: US 8,513,433 B2
(45) Date of Patent: Aug. 20, 2013

(54) SMALL MOLECULE INHIBITORS OF PARP ACTIVITY

(75) Inventors: Bijoy Panicker, Holbrook, NY (US); Dong Sung Lim, Rochelle Park, NJ (US); David E. Smith, Sea Cliff, NY (US)

(73) Assignee: Angion Biomedica Corp., Uniondale, NY (US)

( * ) Notice: Subject to any disclaimer, the term of this patent is extended or adjusted under 35 U.S.C. 154(b) by 0 days.

(21) Appl. No.: 13/381,856

(22) PCT Filed: Jul. 2, 2010

(86) PCT No.: PCT/US2010/001893
§ 371 (c)(1),
(2), (4) Date: Mar. 30, 2012

(87) PCT Pub. No.: WO2011/002520
PCT Pub. Date: Jan. 6, 2011

(65) Prior Publication Data
US 2012/0184533 A1      Jul. 19, 2012

Related U.S. Application Data

(60) Provisional application No. 61/270,101, filed on Jul. 2, 2009.

(51) Int. Cl.
*A61K 31/4184* (2006.01)
*C07D 403/04* (2006.01)
*C07D 401/04* (2006.01)

(52) U.S. Cl.
USPC ........ 548/306.1; 540/476; 540/593; 546/144; 546/165; 514/183; 514/213.01; 514/307; 514/314; 514/394

(58) Field of Classification Search
USPC ....... 540/476, 593; 546/144, 165; 548/306.1
See application file for complete search history.

(56) References Cited

U.S. PATENT DOCUMENTS 6,696,437 B1 * 2/2004 Lubisch et al. .......... 514/217.09

FOREIGN PATENT DOCUMENTS

| WO | WO 00/32579 A2 | 6/2000 |
| WO | WO 01/21615 | 3/2001 |
| WO | WO 2006/110816 A1 | 10/2006 |
| WO | WO-2009/079011 A1 * | 6/2009 |

OTHER PUBLICATIONS

Golub et al., Science, vol. 286, Oct. 15, 1999, pp. 531-537.*
International Search Report for PCT/US2010/001893, dated Apr. 1, 2011 (published as WO 2011/002520 on Jan. 6, 2011).

* cited by examiner

*Primary Examiner* — Laura L. Stockton
(74) *Attorney, Agent, or Firm* — Michael A. Yamin

(57) ABSTRACT

Compounds and pharmaceutical compositions are provided that inhibit the activity of poly ADP-ribose synthetase (PARP). Such compounds are useful in the treatment of various diseases, conditions and injuries such as stroke, myocardial infarction, ischemia-perfusion injury in various organs, traumatic brain injury, atherosclerosis, inflammatory diseases and cancer.

21 Claims, No Drawings

SMALL MOLECULE INHIBITORS OF PARP ACTIVITY

This application is a U.S. national phase application under 35 U.S.C. §371 of international PCT application number PCT/US2010/001893, filed Jul. 2, 2010, incorporated herein by reference in its entirety, which claims priority to U.S. provisional application Ser. No. 61/270,101, filed Jul. 2, 2009.

GOVERNMENT SUPPORT

This invention was made with government support under Grant No. NS062625 awarded by the National Institutes of Health. The government has certain rights in the invention.

BACKGROUND OF THE INVENTION

Poly ADP-ribose synthetase 1 (or PARP-1) is a dimeric nuclear protein, with two 113 kDa polypeptide subunits, each consisting of three functional domains: the DNA binding amino terminal domain with two zinc fingers for recognition of single and double strand DNA breaks, such as those induced by reactive oxygen species (ROS), gamma-irradiation and DNA alkylating agents, the central automodification domain (auto ADP-ribosylation), and the carboxyl terminus catalytic domain, using NAD+ as substrate, for the synthesis of the ADP-ribose polymers, which vary in length between 50-200 subunits. Other family members, all of which share high homology to PARP-1 in the amino and carboxyl termini are PARP-2, 3, vault-PARP and tankyrase. In addition to autocatalytic ADP-ribosylation, PARP-1 has been shown to use histones, topoisomerase I and II, DNA polymerases, and DNA ligase 2 as protein acceptors. This poly ADP-ribosylation appears to inhibit the activity of some of the enzymes, but for histones the ADP-ribosylation has been proposed to stimulate chromosome relaxation allowing for DNA repair. In fact, a requirement for PARP-1 in the recovery from DNA damage induced by N-methyl-N-nitrosourea (MNU) and gamma-radiation was demonstrated using PARP deficient mice and embryo fibroblasts.

Importantly, reactive oxygen species (ROS) have been shown to mediate over-activation of PARP-1, which has been demonstrated to cause critical ATP depletion leading to cell necrosis, as the toxic effects can be substantially ameliorated by either: PARP-1 inhibitors in the cell lineages; macrophages, aortic smooth muscle, neuronal and endothelial, or absence of active PARP-1 in PARP-1−/− deficient fibroblasts.

In addition to the role of PARP-1 in a housekeeping, general genome maintenance function, there is more recent evidence for a role of PARP-1 in specific gene expression, particularly through interaction with Nf-κB. Importantly in the context of ischemia-reperfusion (IR) injury, target genes of Nf-κB in endothelial cells include inducible nitric-oxide synthase (iNOS) and the cell adhesion molecules P-selectin and intracellular adhesion molecule-1 (ICAM-1). Nitric oxide (NO), which is known to have potent vasodilating activity may act as a protective factor during IR injury, however under in the presence of superoxide, endogenous NO has been shown to be detrimental to the health of the IR injured tissues, possibly due to the synthesis of peroxynitrite. In turn, the cell surface expression of P-selectin and ICAM-1 has been shown to mediate the tissue infiltration of neutrophils, which has been demonstrated to contribute to IR-mediated organ damage. PARP-1 deficient mice have been shown to be resistant to the ischemia reperfusion injury of the heart, which is associated with reduced level of ICAM-1 and P-selectin expression in the vascular endothelium and injured myocytes of the myocardium and corresponding neutrophil recruitment induced by ischemia-reperfusion.

Several studies of the use of pharmacological inhibitors of PARP-1 in vivo have demonstrated efficacy in reducing IR induced tissue damage, and improved function of the heart, skeletal muscle, liver and arthritic joints. In a rabbit model, PARP-1 inhibitors significantly decreased infarct size in the heart due to 45-minute occlusion and two-hour reperfusion, as well as skeletal muscle necrosis due to a two-hour occlusion and four-hour reperfusion. In a study of liver microcirculation and function after hemorrhagic shock and resuscitation in rats, the PARP-1 inhibitor 5-aminoisoquinoline (5-AIQ), demonstrating decreased leukocyte-endothelial interaction, decreased liver injury and improved liver function. Also, in a mouse model of arthritis, the PARP-1 inhibitor 5-iodo-6-amino-1,2-benzopyrone (INH2BP) reduced the severity of the disease as assessed by the histological parameters; inflammatory cell infiltration, hyperplasia of the synovium and tissue necrosis.

Several studies in animal models of ischemia-reperfusion have been performed specifically to elucidate the possible role of over-activated PARP-1 in the tissue injury. In a mouse model of thoracoabdominal aneurysm mediated renal injury, the potent PARP-1 inhibitor PJ34 was used to determine the possible role of PARP-1 in this setting. Mice were exposed to eleven minutes of aortic ischemia followed by 48 hours of reperfusion, and were treated with PJ34 1 hour before and immediately after the ischemic period. PJ34 was shown to preserve renal mitochondrial activity and decrease steady state levels of a marker for neutrophil infiltration, but had no apparent affect on fibrinolysis stimulated by the ischemia-reperfusion. Studies in a rat model of direct renal ischemia induced by occluding the renal arteries, demonstrated that the PARP-1 inhibitors 3-aminobenzamide (3-AB) and 1,5-dihroxyisoquinoline improved kidney function as measured by blood and urine markers, plasma urea, plasma creatinine and glomerular filtration rate following 45 minutes of ischemia and up to six hours of reperfusion, with the experimental drugs given one minute before reperfusion. Finally, in the study of PARP-1 expression in human transplant recipients between days 5 and 11 of post-transplantation, all with acute tubular necrosis; PARP-1 expression correlated with the duration of cold renal ischemia, with its expression being highest after ten hours and correlating significantly with delayed renal function.

Familial breast and ovarian cancers, which account for 5-10% of these cancers, are commonly caused by the inherited defect in one of the BRCA1 or BRCA2 alleles. During life the normal, functional BRCA1 or BRCA2 alleles can be lost in some cells, thus initiating the development of a tumor. The tumors that developed were BRCA1 or BRCA2 deficient while remaining somatic cells had functional BRCA proteins. As described above, such tumor cells would be expected to be extremely sensitive to PARP-1 inhibition and this has been confirmed recently. Two independent groups demonstrated specific killing of BRCA deficient cells and inhibition of tumor xenograft growth by pharmacological inhibition of PARP-1 alone with no requirement to combine with chemotherapy. In addition cells deficient in other gene products responsible for homologous recombination such as RAD51, RAD54, DSS1, RPA1, NBSI ATM, ATR CHK1, FANCD2, FANCA or FANCC, are also sensitive to PARP-1 inhibition.

Alternatively, for the majority of neoplasias, which are not deficient in HR function; the combination of DNA damaging agents (chemotherapy or radiation treatment) with PARP-1 inhibition would be expected to mimic the PARP-1 deficient animal studies and increase the tumor's sensitivity to the DNA damaging agent, and this has been the case. Synergistic tumor cell killing has been demonstrated using a PARP-1 inhibitor in combination with camptothecin, a topoisomerase I inhibitor; with the PARP-1 inhibitor increasing cytotoxicity and DNA strand breaks in parallel, 2.5 fold. Consistent with this, camptothecin alone induced DNA strand breaks that lead to a four-fold activation of PARP-1. Interestingly, etoposide, a topoisomerase II inhibitor, induced DNA strand breaks but failed to induce PARP-1 or synergize with the PARP-1 inhibitor in cytotoxicity. Similarly, PARP-1 deficient V79 cells were shown to be hypersensitive to topoisomerase I inhibitors but resistant to etoposide. Also, PARP-1 inhibitors could not potentiate the cytotoxicity of cisplatin in ovarian tumor cells, again suggesting specificity to the type of strand breaks. Several studies have shown the potentiation of temozolomide (TMZ) by PARP-1 inhibitors. Studies have demonstrated the potentiation (1.2-5 fold) of TMZ growth inhibition and cytotoxicity by PARP-1 pharmacological inhibition across many tumor cell lines representing lung, ovarian, colon and breast cancers (gliomas not tested in their system). PARP-1 inhibition was shown to increase the antitumor activity of TMZ against intracranial melanoma, lymphoma, and glioma in vivo using murine orthotopic, tumor models; demonstrating improved survival of tumor bearing mice and an increase in anti-metastatic effect of TMZ. Also, other studies have shown that PARP-1 inhibition increased the antiproliferative effect of TMZ in colorectal cancer cell line LoVo by 5.5 fold, and decreased recovery from gamma-radiation damage in this cell line by 75%. In vivo, a non-toxic dose of this inhibitor increased the delay of LoVo xenograft growth induced by irinotecan, TMZ and x-irradiation by two- to threefold. Interestingly, increased antitumor activity was demonstrated from PARP-1 inhibition with TMZ in another colorectal line, SW620 xenografts while no such activity was demonstrated in vitro. Further analysis demonstrated PARP-1 inhibition statistically, significantly increased blood flow to the tumor and thus possibly increased TMZ delivery to the SW620 xenografts. This possible utility of PARP-1 inhibitors in cancer therapy has been described earlier for the less potent PARP-1 inhibitor nicotinamide, which had been shown to inhibit contraction of vascular smooth muscle cells in tumors. Activation of the transcription factor, NF-κB which has been shown in many tumor cell lines, including glioma, in vitro and in vivo to promote cell survival, proliferation, angiogenesis and metastasis, by transcriptional activation of antiapoptotic genes (e.g., cIAP, survivin, Bcl-2 and Bcl-X1) cell cycle regulatory genes (cyclin D1 and c-myc) COX-2, matrix meltalloproteinase-9 (MMP-9) and vascular endothelial growth factor (VEGF). As described above, the role of PARP-1 in activation of NF-κB and the benefit of inhibitors of PARP-1 activity also have relevance in cancer therapy.

In certain embodiments, the present invention is directed toward the identification of small organic molecules that exhibit PARP inhibitory activity and are thus useful in the treatment or prevention of conditions or diseases in which inhibition of PARP is desirable.

All citations in the present application are incorporated herein by reference in their entireties. The citation of any reference herein should not be construed as an admission that such reference is available as "Prior Art" to the instant application.

SUMMARY OF THE INVENTION

As discussed above, there remains a need for the development of novel therapeutics that inhibit PARP activity.

In one embodiment, certain novel inventive compounds have the structure shown in Formula (I) below:

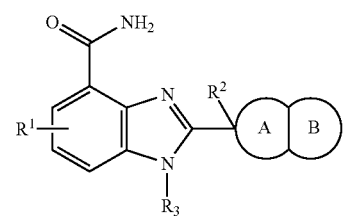

wherein $R^1$ is one or more H, hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkynyl, optionally substituted aliphatic, alicyclic, heteroaliphatic, or heterocyclic;

$R^2$ is H, optionally substituted alkyl or cycloalkyl;

$R^3$ is H, $COR^4$, $CONR^4R^5$, $COOR^4$, $SO_2R^4$, optionally substituted alkyl, alkenyl, alkynyl, cyclolalkyl, heterocycloalkyl, aryl or heteroaryl;

$R^4$ and $R^5$ are independently selected from the group consisting of H, OH, $NH_2$, alkyl, alkenyl, alkynyl, cycloalkyl, heterocycloalkyl, aryl, or heteroaryl;

A and B joined together form a bicyclic ring wherein:

A is nonaromatic 4, 5, 6, 7 or 8-membered ring that contains 1 or 2 nitrogen atoms and optionally one sulfur or oxygen atom, where in the nonaromatic ring is optionally substituted with 1, 2 or 3 substituents selected from the group consisting of hydroxy, halogen, cyano, $OR^4$, nitro, $NH_2$, $NR^4R^5$, $NR^4COR^5$, $NR^4SO_2R^4$, $CONR^4R^5$, $COOR^4$, $SO_2R^4$, alkyl, alkenyl, alkynyl, alkoxyalkyl, alkoxycarbonylalkyl, cycloalkyl, cycloalkylalkyl, haloalkyl, heterocycle, heterocycloalkyl, aryl, arylalkyl, heteroaryl, heteroarylalkyl or oxo; and B is aryl or heteroaryl that is optionally substituted with 1, 2 or 3 substituents selected from the group consisting of hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkyl, alkenyl, alkynyl, alkoxyalkyl, alkoxycarbonylalkyl, cycloalkyl, cycloalkylalkyl, haloalkyl, heterocycle, heterocycloalkyl, aryl, arylalkyl, heteroaryl, or heteroarylalkyl.

In another embodiment, certain novel inventive compounds have the structure shown in Formula (II) below:

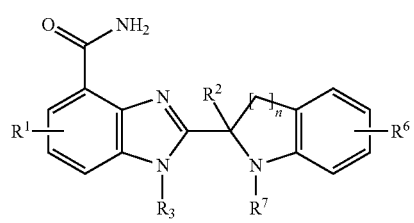

wherein $R^1$ and $R^6$ are one or more H, hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkynyl, optionally substituted aliphatic, alicyclic, heteroaliphatic or heterocyclic;

$R^2$ is H, optionally substituted alkyl or cycloalkyl;

$R^3$ and $R^7$ are independently selected from the group consisting of H, $COR^4$, $CONR^4R^5$, $COOR^4$, $SO_2R^4$, optionally substituted alkyl, alkenyl, alkynyl, cyclolalkyl, heterocycloalkyl, aryl or heteroaryl;

$R^4$ and $R^5$ are independently selected from the group consisting of H, OH, $NH_2$, alkyl, alkenyl, alkynyl, cycloalkyl, heterocycloalkyl, aryl, or heteroaryl; and n=0, 1, 2, 3 or 4.

In another embodiment, certain novel inventive compounds have the structure shown in Formula (III) below:

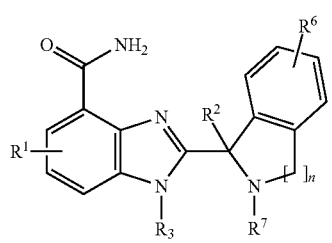

III wherein $R^1$ and $R^6$ are one or more H, hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkynyl, optionally substituted aliphatic, alicyclic, heteroaliphatic or heterocyclic;

$R^2$ is H, optionally substituted alkyl or cycloalkyl;

$R^3$ and $R^7$ are independently selected from the group consisting of H, $COR^4$, $CONR^4R^5$, $COOR^4$, $SO_2R^4$, optionally substituted alkyl, alkenyl, alkynyl, cyclolalkyl, heterocycloalkyl, aryl or heteroaryl;

$R^4$ and $R^5$ are independently selected from the group consisting of H, OH, $NH_2$, alkyl, alkenyl, alkynyl, cycloalkyl, heterocycloalkyl, aryl, or heteroaryl; and n=0, 1, 2, 3 or 4.

In a further embodiment, certain novel inventive compounds have the structure shown in Formula (IV) below:

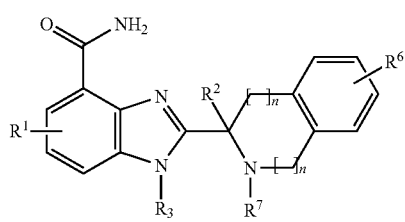

IV wherein $R^1$ and $R^6$ are one or more H, hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkynyl, optionally substituted aliphatic, alicyclic, heteroaliphatic or heterocyclic;

$R^2$ is H, optionally substituted alkyl or cycloalkyl;

$R^3$ and $R^7$ are independently selected from the group consisting of H, $COR^4$, $CONR^4R^5$, $COOR^4$, $SO_2R^4$, optionally substituted alkyl, alkenyl, alkynyl, cyclolalkyl, heterocycloalkyl, aryl or heteroaryl;

$R^4$ and $R^5$ are independently selected from the group consisting of H, OH, $NH_2$, alkyl, alkenyl, alkynyl, cycloalkyl, heterocycloalkyl, aryl, or heteroaryl; and n=0, 1, 2 or 3.

In another aspect, the invention is directed to compositions including pharmaceutical compositions comprising of any of the compounds disclosed herein.

In another aspect, the invention provides methods for the use of any of the compounds disclosed herein for inhibiting PARP activity in a patient or a biological sample. The compounds and pharmaceutical compositions of the invention have the activity of inhibiting PARP and are useful in the treatment of any disease, disorder or condition in which inhibition of PARP activity would be useful.

In another aspect, the invention provides methods for the use of any of the compounds disclosed herein for treating or lessening the severity of a disease, disorder or condition associated with PARP activity. Such diseases, disorders and conditions include, but are not limited to, muscular dystrophy, hepatic ischemia-reperfusion injury, cerebral infarction, ischemic heart disease, damaged and/or ischemic organs, transplants or grafts; ischemia/reperfusion injury; stroke, traumatic head injury, spinal cord injury, and other cerebrovascular diseases; myocardial ischemia; atherosclerosis; peripheral vascular disease; other cardiovascular diseases; diabetes; renal failure; pancreatitis; multiple sclerosis; and neurodegenerative diseases such as Parkinsonism and Alzheimer disease. In certain exemplary embodiments, the method is for the treatment of wounds for acceleration of healing; amelioration of ischemia/reperfusion injury in the brain, heart, liver, kidney, or other tissues or organs; normalization of myocardial perfusion as a consequence of chronic cardiac ischemia or myocardial infarction; renal failure secondary to chronic diabetes and/or hypertension; and/or diabetes mellitus. Use of the compound is also provided for prophylaxis or preventing the occurrence of the diseases in subjects, and in particular subjects susceptible to of exhibiting risk factors for, the aforementioned diseases and conditions.

Furthermore, compounds embodied herein are also useful for the treatment of various dysproliferative diseases and in particular for potentiating the activity of chemotherapeutic agents against dysproliferative diseases. Such dysproliferative diseases include but are not limited to various cancers, as well as inflammatory disease in particular where inflammation, especially chronic inflammation, leads to inappropriate vascularization. Examples of cancers, tumors, malignancies, neoplasms, and other dysproliferative diseases that can be treated according to the invention include leukemias, such as myeloid and lymphocytic leukemias, lymphomas, myeloproliferative diseases, and solid tumors, such as but not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. In preferred but non-limiting embodiments, brain tumors, including glioma, and pancreatic cancers are amenable to treatment by the compounds of the present invention.

The invention also provides methods for the use of any of the compounds disclosed herein for use as adjuvant therapy with DNA-damaging chemotherapeutics for treatment of various forms of cancer including but not limited melanoma, breast, ovarian and glioblastoma and in treatment of HIV infection. Use of the compound is also provided for prophylaxis or preventing the occurrence of the diseases in subjects, and in particular subjects susceptible to of exhibiting risk factors for, the aforementioned diseases and conditions.

Examples of inflammatory diseases toward which compounds of the invention have benefit include rheumatoid arthritis, atherosclerosis, and neovascularization in the eye as a consequence of diabetic retinopathy.

The present invention is also directed to treatment of non-malignant tumors and other disorders involving inappropriate cell or tissue growth by administering a therapeutically effective amount of an agent of the invention. For example, the invention is useful for the treatment of arteriovenous (AV) malformations, particularly in intracranial sites. The invention can also be used to treat psoriasis, a dermatologic condition that is characterized by inflammation and vascular proliferation; benign prostatic hypertrophy, a condition associated with inflammation and possibly vascular proliferation; and cutaneous fungal infections. Treatment of other hyperproliferative disorders is also embraced herein. The agents may also be used topically to remove warts, birthmarks, moles, nevi, skin tags, lipomas, angiomas including hemangiomas, and other cutaneous lesions for cosmetic or other purposes.

In another embodiment, a method is provided that comprises the step of administering to a subject suffering from a disease or condition associated with PARP activity an effective amount of a compound of any one of formulas (I)-(IV) or a composition thereof; wherein the compound is characterized by its ability to inhibit PARP activity. In a further embodiment, the disease or condition can be muscular dystrophy, hepatic ischemia-reperfusion injury, cerebral infarction, ischemic heart disease, damaged and/or ischemic organs, transplants or grafts; ischemia/reperfusion injury; stroke, traumatic head injury, spinal cord injury, and other cerebrovascular diseases; myocardial ischemia; atherosclerosis; peripheral vascular disease; other cardiovascular diseases; diabetes; renal failure; multiple sclerosis; and neurodegenerative diseases such as Parkinsonism and Alzheimer disease. In certain exemplary embodiments, the method is for the treatment of wounds for acceleration of healing; amelioration of ischemia/reperfusion injury in the brain, heart, liver, kidney, or other tissues or organs; normalization of myocardial perfusion as a consequence of chronic cardiac ischemia or myocardial infarction; renal failure secondary to chronic diabetes and/or hypertension; and/or diabetes mellitus. In other embodiments the disease or condition is a dysproliferative disease such as cancer. In another embodiment the disease is an inflammatory disease. In another embodiment, the compound inhibits PARP with an in vitro $IC_{50}$ of about 1 to about 5 micromolar. In another embodiment, the compound inhibits PARP with an in vitro $IC_{50}$ of about 0.1 to about 1 micromolar. In another embodiment, the compound inhibits PARP with an in vitro $IC_{50}$ of about 0.001 to about 0.1 micromolar. In another embodiment the compound inhibits PARP with an in vitro $IC_{50}$ of more than about 0.001 micromolar. In another embodiment, the compound inhibits PARP with an in vitro $IC_{50}$ of about 0.001 micromolar.

Definitions

It is understood that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbanked, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. Examples of substituents include, but are not limited to aliphatic; heteroaliphatic; alicyclic; heterocyclic; aromatic, heteroaromatic; aryl; heteroaryl; alkylaryl; aralkyl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons as defined by IUPAC, which are optionally substituted with one or more functional groups. As defined herein, "aliphatic" is intended to include optionally substituted alkyl, alkenyl and alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms. In some instances aliphatic can include alicyclic or cycloalkyl, including unsaturations therein.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargy 1), 1-propynyl and the like.

The term "alicyclic", as used herein, refers to compounds that combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl, cyclohexyl, —$CH_2$-cyclohexyl, cyclohexenylethyl, cyclohexanylethyl, norbornyl moieties and the like, which again, may bear one or more substituents.

The term "cycloalkyl", as used herein, refers to cyclic alkyl groups, specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like. Additional examples of generally applicable substituents are illustrated by the specific embodiments shown in the Examples that are described herein.

The term "heteroaliphatic", as used herein, refers to aliphatic moieties in which one or more carbon atoms in the main chain have been replaced with a heteroatom. Thus, a heteroaliphatic group refers to an aliphatic chain which contains one or more oxygen, sulfur, nitrogen, phosphorus or silicon atoms in place of carbon atoms in the aliphatic main chain. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)$NR^{G3}$—, —C(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocyclic" refers to a non-aromatic 5-, 6- or 7-membered ring or a polycyclic group, including, but not limited to a bi- or tricyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one or more hydrogen atoms thereon with aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; or —$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic". Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring having p-orbitals perpendicular to the plane of the ring at each ring atom, and satisfying the Huckel rule where the number of pi electrons in the ring is (4n+2) wherein n is an integer. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, -(heteroaliphatic)heteroaromatic, -(alkyl)aromatic, -(heteroalkyl)aromatic, -(alkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. In some instances corresponding moieties may be referred to synonymously as aralkyl, heteroaralkyl and the like. Substituents include, but are not limited to, any of the previously mentioned substituents, i.e., the substituents recited for aliphatic moieties, or for other moieties as disclosed herein, resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

As defined herein, "aryl" and "heteroaryl" groups (including bicyclic aryl groups) can be unsubstituted or substituted, wherein substitution includes replacement of one or more of the hydrogen atoms thereon independently with any of the previously mentioned substitutents, i.e., the substituents recited for aliphatic moieties, or for other moieties as disclosed herein, resulting in the formation of a stable compound. For example, aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; heteroaliphatic; alicyclic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^2$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy, include but are not limited to, methoxy, ethoxy, propoxy, isopropoxy, n-butoxy, i-butoxy, sec-butoxy, tent-butoxy, neopentoxy, n-hexoxy and the like.

The term "thioalkyl" as used herein refers to a saturated (i.e., S-alkyl) or unsaturated (i.e., S-alkenyl and S-alkynyl)

group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thioalkyl include, but are not limited to, methylthio, ethylthio, propylthio, isopropylthio, n-butylthio, and the like.

The term "alkylamino" refers to a group having the structure —NHR' wherein R' is aliphatic or alicyclic, as defined herein. The term "aminoalkyl" refers to a group having the structure $NH_2R'$—, wherein R' is aliphatic or alicyclic, as defined herein. In certain embodiments, the aliphatic or alicyclic group contains 1-20 aliphatic carbon atoms. In certain other embodiments, the aliphatic or alicyclic group contains 1-10 aliphatic carbon atoms. In still other embodiments, the aliphatic or alicyclic group contains 1-6 aliphatic carbon atoms. In yet other embodiments, the aliphatic or alicyclic group contains 1-4 aliphatic carbon atoms. In yet other embodiments, R' is an alkyl, alkenyl, or alkynyl group containing 1-8 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(=O)$R_x$; —$CO_2(R_x)$; —C(=O)N($R_x)_2$; —OC(=O)$R_x$; —$OCO_2R_x$; —OC(=O)N($R_x)_2$; —N($R_2)_2$; —$OR_x$; —$SR_x$; —S(O)$R_x$; —$S(O)_2R_x$; —$NR_x$(CO)$R_x$; —N($R_x$)$CO_2R_x$; —N($R_x$)S(O)$_2R_x$; —N($R_x$)C(=O)N($R_x)_2$; —$S(O)_2N(R_x)_2$; wherein each occurrence of $R_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—$NH_2$), secondary (—$NHR_x$), tertiary (—$NR_xR_y$) or quaternary (—$N^+R_xR_yR_z$) amine, where $R_x$, $R_y$ and $R_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "$C_{2-6}$alkenylene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Another example is an N-methyl derivative of a compound, which is susceptible to oxidative metabolism resulting in N-demethylation. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The term "tautomerization" refers to the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The term "tautomer" as used herein, refers to the compounds produced by the proton shift.

By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-alkyl and N-aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective. Groups in Organic Synthesis" Third Ed. Greene, T. W. and Wuts, P. G., Eds., John Wiley & Sons, New York: 1999, the entire contents of which are hereby incorporated by reference.

As used herein, the term "isolated" when applied to the compounds of the present invention, refers to such compounds that are (i) separated from at least some components with which they are associated in nature or when they are made and/or (ii) produced, prepared or manufactured by the hand of man.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof; or purified versions thereof. For example, the term "biological sample" refers to any solid or fluid sample obtained from, excreted by or secreted by any living organism, including single-celled microorganisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, seminal fluid, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DETAILED DESCRIPTION OF CERTAIN PREFERRED EMBODIMENTS OF THE INVENTION

Ischemia-reperfusion injury resulting in acute tubular necrosis is a major contributing factor for kidney dysfunction, and can be caused by extra renal surgery, such as the repair of a thoracoabdominal aneurysm or cardio-pulmonary bypass, leading to hypovolemic shock to the kidney, and in the setting of kidney transplantation. In fact, in complex thoracoabdominal surgery, associated renal dysfunction is an independent predictor of operative mortality, increasing it approximately 3 fold. In the United States, in November 2006 there are 69,000 patients on the waiting list for a kidney transplant, and of the 9,270 donor kidneys recovered as reported through August of this year, 4,865 from deceased donors (Organ Procurement and Transplantation Network, OPTN). The observation that the success of cadaver donors transplantation is consistently worse than living unrelated or one haplotype-matched living-related donors must be based on nonspecific, antigen-independent variables, with one such factor, ischemia-reperfusion injury may be the most important. In fact, about 20-30% of the cadaver-donor kidneys suffer from delayed graft function, due to acute tubular necrosis. As more organs are removed from "marginal" or "extended" donors (i.e. aged>60 years, with hypertension, acute tubular necrosis etc.) as there has been an upward trend in the use of cadaver-donor kidneys in the past two years (OPTN), these rates of delayed renal function and ultimately graft failure may increase due to antigen-independent factors associated with ischemia-reperfusion injury. Long-term graft behavior may also be influenced by this initial ischemia-reperfusion injury leading to poor graft function as reported in patients 1 and 5 years post-transplant. Also, the duration of storage of these cadaver-donor kidneys appears to contribute to the severity of this initial ischemia-reperfusion injury, as reported by Salahudeen and colleagues in their retrospective analysis of 6465 kidney transplant patients in which that prolonged cold ischemia was shown to be a significant predictor of long-term graft loss.

The pathophysiology of ischemia-reperfusion injury of the kidney is manifested by two major events: a significant reduction in glomerular filtration rate by as much as 95%, and the reduction of renal blood flow to 50% of normal. Though the degree of damage will increase with the duration of cold or warm ischemia, microscopic evaluation of the outer medulla after 45-60 minutes of warm ischemia reveals extensive necrosis of the third (S3) segment of the proximal tubule with associated interstitial edema, tubular dilation, tubular flattening and luminal obstructions. The underlying changes to the metabolism of the oxygen-deprived tubule cells through this process of ischemia and reperfusion are as follows; during the period of ischemia, which rapidly damages metabolically active cells, oxidative metabolism is greatly reduced while anaerobic metabolism continues. The disruption of mitochondrial oxidative phosphorylation leads to a rapid decrease in cellular ATP and NAD/NADH levels, and ATP is rapidly dephosphorylated to adenosine monophosphate, which in turn is degraded to hypoxanthine. ATP depletion causes the degradation of ATP-dependent ion channels leading to the passive shift of ions: $K^+$ and $Mg^{++}$ diffuse out of the cells while $Na^+$, $Ca^{++}$ and $H_2O$ flow down the concentration gradient into the cell, causing cell swelling and the conversion of xanthine dehydrogenase to (HDH) to xanthine oxidase (XO) by a calcium dependent protease. In addition, anaerobic metabolism during ischemia also induces free $Fe^{++}$ cellular levels, $Fe^{++}$ being an important catalyst in the reactions forming free radicals during reperfusion. During reperfusion, XO and $Fe^{++}$ catalyze the formation of the reactive oxygen species (ROS)$O_2.^-$, $H_2O_2$ and $OH.^-$. Also, the kidney vascular endothelium is a major source of nitric oxide (NO), and following reperfusion this endothelial cell derived NO has been shown to react with $O_2.^-$ to form the potent oxidant ONOO— (peroxynitrite). These toxic, reactive oxygen molecules cause lipid peroxidation, DNA damage, protein denaturation, and altered membrane transport proteins and necrotic cell death.

The evidence for the presence of, and the direct role of, ROS in ischemia-reperfusion injury in the kidney are the results in animal studies demonstrating Ischemia-reperfusion increased production of lipid peroxidation, which appeared within minutes of reperfusion. Also, Green and colleagues demonstrated that the lipid peroxidation did not occur during prolonged hypothermic kidney storage in a rabbit transplantation model, only appearing with reperfusion. Finally introduction of the superoxide scavenger, superoxide dismutase (SOD) via adenovirus mediated expression in recipient rats, and of a randomized clinical study of intravenous administration of recombinant SOD at the time of transplantation of cadaveric kidney demonstrated beneficial effect. In the rat study, ischemia-reperfusion injury was lessened by SOD transgene expression as measured by lessening of tubular injury, decreased infiltration of leukocytes and improved glomerular filtration rate. In the clinical study, although not shown to cause an immediate improvement in renal function, SOD administration was associated with improved long-term graft survival.

As mentioned above, ROS have been shown to mediate over-activation of PARP-1, which has been demonstrated to cause critical ATP depletion leading to cell necrosis, as the toxic effects can be substantially ameliorated by either: PARP-1 inhibitors in the cell lineages; macrophages, aortic smooth muscle, neuronal and endothelial, or absence of active PARP-1 in PARP-1–/– deficient fibroblasts.

Human malignant gliomas (astrocytomas and glioblastomas) are the most commonly diagnosed primary CNS tumors, with 20,500 new cases and 12,740 deaths estimated by National Cancer Institute for 2007. Despite decades of advances in neurosurgery, radiation therapy, and novel chemotherapeutic regimens, the mean survival time from diagnosis with glioma has been extended only by months with only 5% of patients surviving five years after diagnosis 1-4. This continued high death rate stresses the need for novel therapeutics that could significantly prolong the patient's life and quality of life. In the past few years we have seen FDA approval of several of these novel therapeutics, which target key proteins, which promote tumor growth, angiogenesis, and metastasis; such as GLEEVEC®, AVASTIN®, HERCEPTIN® and TARCEVA®, demonstrating significant therapeutic benefit in a variety of cancers. Unfortunately, malignant gliomas have proven refractory to significant therapeutic benefit by such molecular-targeted agents, still leaving us with the critical need for better therapies. Compounds embodied herein can be used in combination with and to improve the efficacy of radiation therapy and chemotherapeutic regimens already used for glioma as well as with other cancers.

Familial breast and ovarian cancers, which account for 5-10% of these cancers, are commonly caused by the inherited defect in one of the BRCA 1 or BRCA2 alleles. During life the normal, functional BRCA1 or BRCA2 alleles can be lost in some cells, thus initiating the development of a tumor. The tumors that developed were BRCA1 or BRCA2 deficient while remaining somatic cells had functional BRCA proteins. As described above, such tumor cells would be expected to be extremely sensitive to PARP-1 inhibition and this has been confirmed recently. Two independent groups demonstrated specific killing of BRCA deficient cells and inhibition of tumor xenograft growth by pharmacological inhibition of PARP-1 alone with no requirement to combine with chemotherapy.

The foregoing target diseases and conditions are merely illustrative of the plethora of diseases and conditions for which the compounds embodied herein are useful therapeutically or prophylactically, as enumerated elsewhere herein by way of non-limiting example only.

General Description of Compounds of the Invention

In one embodiment, certain novel inventive compounds have the structure shown in Formula (I) below:

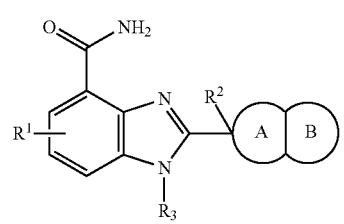

wherein $R^1$ is one or more H, hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkynyl, optionally substituted aliphatic, alicyclic, heteroaliphatic, or heterocyclic;

$R^2$ is H, optionally substituted alkyl or cycloalkyl;

$R^3$ is H, $COR^4$, $CONR^4R^5$, $COOR^4$, $SO_2R^4$, optionally substituted alkyl, alkenyl, alkynyl, cyclolalkyl, heterocycloalkyl, aryl or heteroaryl;

$R^4$ and $R^5$ are independently selected from the group consisting of H, OH, $NH_2$, alkyl, alkenyl, alkynyl, cycloalkyl, heterocycloalkyl, aryl, or heteroaryl;

A and B joined together form a bicyclic ring wherein:

A is nonaromatic 4, 5, 6, 7 or 8-membered ring that contains 1 or 2 nitrogen atoms and optionally one sulfur or oxygen atom, where in the nonaromatic ring is optionally substituted with 1, 2 or 3 substituents selected from the group consisting of hydroxy, halogen, cyano, $OR^4$, nitro, $NH_2$, $NR^4R^5$, $NR^4COR^5$, $NR^4SO_2R^4$, $CONR^4R^5$, $COOR^4$, $SO_2R^4$, alkyl, alkenyl, alkynyl, alkoxyalkyl, alkoxycarbonylalkyl, cycloalkyl, cycloalkylalkyl, haloalkyl, heterocycle, heterocycloalkyl, aryl, arylalkyl, heteroaryl, heteroarylalkyl or oxo; and B is aryl or heteroaryl that is optionally substituted with 1, 2 or 3 substituents selected from the group consisting of hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkyl, alkenyl, alkynyl, alkoxyalkyl, alkoxycarbonylalkyl, cycloalkyl, cycloalkylalkyl, haloalkyl, heterocycle, heterocycloalkyl, aryl, arylalkyl, heteroaryl, or heteroarylalkyl.

In certain embodiments, $R^1$ is H, Cl or F.
In other embodiments, $R^2$ is H, methyl or ethyl.
In other embodiments, $R^3$ is H.
In other embodiments, $R^4$ and $R^5$ are H, methyl or ethyl.
In other embodiments, A and B taken together is indolin-2-yl, isoindolin-1-yl, 1,2,3,4-tetrahydroisoquinolin-1-yl, 1,2,3,4-tetrahydroquinolin-2-yl, 1,2,3,4-tetrahydroisoquinolin-3-yl, 2,3,4,5-tetrahydro-1H-benzo[b]azepin-2-yl, 2,3,4,5-tetrahydro-1H-benzo[c]azepin-3-yl, 2,3,4,5-tetrahydro-1H-benzo[d]azepin-2-yl, 2,3,4,5-tetrahydro-1H-benzo[c]azepin-1-yl, 1,2,3,4,5,6-hexahydrobenzo[b]azocin-2-yl, 1,2,3,4,5,6-hexahydrobenzo[c]azocin-3-yl, 1,2,3,4,5,6-hexahydrobenzo[d]azocin-2-yl, 1,2,3,4,5,6-hexahydrobenzo[c]azocin-1-yl or 1,2,3,4,5,6-hexahydrobenzo[d]azocin-4-yl.

Non-limiting examples of compounds of formula I include benzyl 2-(4-carbamoyl-1H-benzo[d]imidazol-2-yl)indoline-1-carboxylate; 2-(indolin-2-yl)-1H-benzo[d]imidazole-4-carboxamide; tert-butyl 2-(4-carbamoyl-1H-benzo[d]imidazol-2-yl)-3,4-dihydroquinoline-1(2H)-carboxylate; 2-(1,2,3,4-tetrahydroquinolin-2-yl)-1H-benzo[d]imidazole-4-carboxamide; benzyl 1-(4-carbamoyl-1H-benzo[d]imidazol-2-yl)isoindoline-2-carboxylate; 2-(isoindolin-1-yl)-1H-benzo[d]imidazole-4-carboxamide; benzyl 1-(4-carbamoyl-1H-benzo[d]imidazol-2-yl)-3,4-dihydroisoquinoline-2(1H)-carboxylate; 2-(1,2,3,4-tetrahydroisoquinolin-1-yl)-1H-benzo[d]imidazole-4-carboxamide; benzyl 3-(4-carbamoyl-1H-benzo[d]imidazol-2-yl)-3,4-dihydroisoquinoline-2(1H)-carboxylate; 2-(1,2,3,4-tetrahydroisoquinolin-3-yl)-1H-benzo[d]imidazole-4-carboxamide; benzyl 3-(4-carbamoyl-1H-benzo[d]imidazol-2-yl)-3-methyl-3,4-dihydroisoquinoline-2(1H)-carboxylate; 2-(3-methyl-1,2,3,4-tetrahydroisoquinolin-3-yl)-1H-benzo[d]imidazole-4-carboxamide; tert-butyl 7-((tert-butoxycarbonyl)amino)-3-(4-carbamoyl-1H-benzo[d]imidazol-2-yl)-3,4-dihydroisoquinoline-2(1H)-carboxylate; tert-butyl 7-amino-3-(4-carbamoyl-1H-benzo[d]imidazol-2-yl)-3,4-dihydroisoquinoline-2(1H)-carboxylate; tert-butyl (3-(4-carbamoyl-1H-benzo[d]imidazol-2-yl)-1,2,3,4-tetrahydroisoquinolin-7-yl)carbamate; and 2-(7-amino-1,2,3,4-tetrahydroisoquinolin-3-yl)-1H-benzo[d]imidazole-4-carboxamide. Other compounds of Formula (I) include 2-(1,2,3,4,5,6-hexahydrobenzo[b]azocin-2-yl)-1H-benzo[d]imidazole-4-carboxamide; 2-(2,3,4,5-tetrahydro-1H-benzo[b]azepin-2-yl)-1H-benzo[d]imidazole-4-carboxamide; 2-(2-ethylindolin-2-yl)-1H-benzo[d]imidazole-4-carboxamide; 2-(2-methyl-1,2,3,4-tetrahydroquinolin-2-yl)-1H-benzo[d]imidazole-4-carboxamide; 2-(2-methyl-2,3,4,5-tetrahydro-1H-benzo[b]azepin-2-yl)-1H-benzo[d]imidazole-4-carboxamide; 2-(2-methylindolin-2-yl)-1H-benzo[d]imidazole-4-carboxamide; 6-fluoro-2-(indolin-2-yl)-1H-benzo[d]imidazole-4-carboxamide; 2-(2-methyl-1,2,3,4,5,6-hexahydrobenzo[b]azocin-2-yl)-1H-benzo[d]imidazole-4-carboxamide; 2-(1,2,3,4,5,6-hexahydrobenzo[c]azocin-1-yl)-1H-benzo[d]imidazole-4-carboxamide; 2-(1-methyl-1,2,3,4,5,6-hexahydrobenzo[c]azocin-1-yl)-1H-benzo[d]imidazole-4-carboxamide; 2-(1-methyl-1,2,3,4-tetrahydroisoquinolin-1-yl)-1H-benzo[d]imidazole-4-carboxamide; 2-(1-methyl-2,3,4,5-tetrahydro-1H-benzo[c]azepin-1-yl)-1H-benzo[d]imidazole-4-carboxamide; 2-(1-methylisoindolin-1-yl)-1H-benzo[d]imidazole-4-carboxamide; 2-(2,3,4,5-tetrahydro-1H-benzo[c]azepin-1-yl)-1H-benzo[d]imidazole-4-carboxamide; 2-(1,2,3,4,5,6-hexahydrobenzo[c]azocin-3-yl)-1H-benzo[d]imidazole-4-carboxamide; 2-(1,2,3,4,5,6-hexahydrobenzo[d]azocin-2-yl)-1H-benzo[d]imidazole-4-carboxamide; hexahydrobenzo[d]azocin-4-yl)-1H-benzo[d]imidazole-4-carboxamide; 2-(2,3,4,5-tetrahydro-1H-benzo[c]azepin-3-yl)-1H-benzo[d]imidazole-4-carboxamide; 2-(2,3,4,5-tetrahydro-1H-benzo[d]azepin-2-yl)-1H-benzo[d]imidazole-4-carboxamide; 2-(2-methyl-1,2,3,4,5,6-hexahydrobenzo[d]azocin-2-yl)-1H-benzo[d]imidazole-4-carboxamide; 2-(2-methyl-2,3,4,5-tetrahydro-1H-benzo[d]azepin-2-yl)-1H-benzo[d]imidazole-4-carboxamide; 2-(3-ethyl-1,2,3,4-tetrahydroisoquinolin-3-yl)-1H-benzo[d]imidazole-4-carboxamide; 2-(3-ethyl-2,3,4,5-tetrahydro-1H-benzo[c]azepin-3-yl)-1H-benzo[d]imidazole-4-carboxamide; 2-(3-methyl-1,2,3,4,5,6-hexahydrobenzo[c]azocin-3-yl)-1H-benzo[d]imidazole-4-carboxamide; 2-(3-methyl-2,3,4,5-tetrahydro-1H-benzo[c]azepin-3-yl)-1H-benzo[d]imidazole-4-carboxamide; 2-(4-ethyl-1,2,3,4,5,6-hexahydrobenzo[d]azocin-4-yl)-1H-benzo[d]imidazole-4-carboxamide; 2-(4-methyl-1,2,3,4,5,6-hexahydrobenzo[d]azocin-4-yl)-1H-benzo[d]imidazole-4-carboxamide; 6-fluoro-2-(1,2,3,4,5,6-hexahydrobenzo[d]azocin-4-yl)-1H-benzo[d]imidazole-4-carboxamide; 6-fluoro-2-(1,2,3,4-tetrahydroisoquinolin-3-yl)-1H-benzo[d]imidazole-4-carboxamide; and 6-fluoro-2-(2,3,4,5-tetrahydro-1H-benzo[c]azepin-3-yl)-1H-benzo[d]imidazole-4-carboxamide.

In another embodiment, certain novel inventive compounds have the structure shown in Formula (II) below:

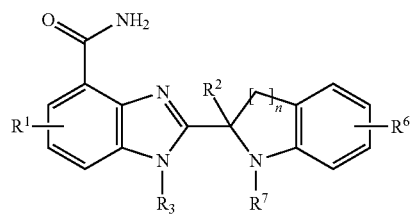

II wherein $R^1$ and $R^6$ are one or more H, hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkynyl, optionally substituted aliphatic, alicyclic, heteroaliphatic or heterocyclic;

$R^2$ is H, optionally substituted alkyl or cycloalkyl;

$R^3$ and $R^7$ are independently selected from the group consisting of H, $COR^4$, $CONR^4R^5$, $COOR^4$, $SO_2R^4$, optionally substituted alkyl, alkenyl, alkynyl, cyclolalkyl, heterocycloalkyl, aryl or heteroaryl;

$R^4$ and $R^5$ are independently selected from the group consisting of H, OH, NH2, alkyl, alkenyl, alkynyl, cycloalkyl, heterocycloalkyl, aryl, or heteroaryl; and n=0, 1, 2, 3 or 4.

In certain embodiments, $R^1$ is H, Cl or F.
In other embodiments, $R^2$ is H, methyl or ethyl.
In other embodiments, $R^3$ is H.
In other embodiments, $R^4$ and $R^5$ are H, methyl or ethyl.
In other embodiments, $R^6$ is H or F.
In other embodiments $R^7$ is H, methyl, ethyl, propyl, isopropyl, t-butyl, cyclopropyl, cyclobutyl, cyclopentyl, 2-fluorobenzyl or phenylethyl.

Non-limiting examples of compound of formula (II) include benzyl 2-(4-carbamoyl-1H-benzo[d]imidazol-2-yl)

indoline-1-carboxylate; 2-(indolin-2-yl)-1H-benzo[d]imidazole-4-carboxamide; tert-butyl 2-(4-carbamoyl-1H-benzo[d]imidazol-2-yl)-3,4-dihydroquinoline-1(2H)-carboxylate; and 2-(1,2,3,4-tetrahydroquinolin-2-yl)-1H-benzo[d]imidazole-4-carboxamide. Other compounds of Formula (II) include 2-(1,2,3,4,5,6-hexahydrobenzo[b]azocin-2-yl)-1H-benzo[d]imidazole-4-carboxamide; 2-(2,3,4,5-tetrahydro-1H-benzo[b]azepin-2-yl)-1H-benzo[d]imidazole-4-carboxamide; 2-(2-ethylindolin-2-yl)-1H-benzo[d]imidazole-4-carboxamide; 2-(2-methyl-1,2,3,4-tetrahydroquinolin-2-yl)-1H-benzo[d]imidazole-4-carboxamide; 2-(2-methyl-2,3,4,5-tetrahydro-1H-benzo[b]azepin-2-yl)-1H-benzo[d]imidazole-4-carboxamide; 2-(2-methylindolin-2-yl)-1H-benzo[d]imidazole-4-carboxamide; 6-fluoro-2-(indolin-2-yl)-1H-benzo[d]imidazole-4-carboxamide; and 2-(2-methyl-1,2,3,4,5,6-hexahydrobenzo[b]azocin-2-yl)-1H-benzo[d]imidazole-4-carboxamide.

In another embodiment, certain novel inventive compounds have the structure shown in Formula (III) below:

III wherein $R^1$ and $R^6$ are one or more H, hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkynyl, optionally substituted aliphatic, alicyclic, heteroaliphatic or heterocyclic;

$R^2$ is H, optionally substituted alkyl or cycloalkyl;

$R^3$ and $R^7$ are independently selected from the group consisting of H, $COR^4$, $CONR^4R^5$, $COOR^4$, $SO_2R^4$, optionally substituted alkyl, alkenyl, alkynyl, cyclolalkyl, heterocycloalkyl, aryl or heteroaryl;

$R^4$ and $R^5$ are independently selected from the group consisting of H, OH, NH2, alkyl, alkenyl, alkynyl, cycloalkyl, heterocycloalkyl, aryl, or heteroaryl; and n=0, 1, 2, 3 or 4.

In certain embodiments, $R^1$ is H, Cl or F.
In other embodiments, $R^2$ is H, methyl or ethyl.
In other embodiments, $R^3$ is H.
In other embodiments, $R^4$ and $R^5$ are H, methyl or ethyl.
In other embodiments, $R^6$ is H or F.
In other embodiments $R^7$ is H, methyl, ethyl, propyl, isopropyl, t-butyl, cyclopropyl, cyclobutyl, cyclopentyl, 2-fluorobenzyl or phenylethyl.

Non-limiting examples of compounds of formula (III) include benzyl 1-(4-carbamoyl-1H-benzo[d]imidazol-2-yl)isoindoline-2-carboxylate; 2-(isoindolin-1-yl)-1H-benzo[d]imidazole-4-carboxamide; benzyl 1-(4-carbamoyl-1H-benzo[d]imidazol-2-yl)-3,4-dihydroisoquinoline-2(1H)-carboxylate; and 2-(1,2,3,4-tetrahydroisoquinolin-1-yl)-1H-benzo[d]imidazole-4-carboxamide. Other compounds of Formula (III) include 2-(1,2,3,4,5,6-hexahydrobenzo[c]azocin-1-yl)-1H-benzo[d]imidazole-4-carboxamide; 2-(1-methyl-1,2,3,4,5,6-hexahydrobenzo[c]azocin-1-yl)-1H-benzo[d]imidazole-4-carboxamide; 2-(1-methyl-1,2,3,4-tetrahydroisoquinolin-1-yl)-1H-benzo[d]imidazole-4-carboxamide; 2-(1-methyl-2,3,4,5-tetrahydro-1H-benzo[c]azepin-1-yl)-1H-benzo[d]imidazole-4-carboxamide; 2-(1-methylisoindolin-1-yl)-1H-benzo[d]imidazole-4-carboxamide; and 2-(2,3,4,5-tetrahydro-1H-benzo[c]azepin-1-yl)-1H-benzo[d]imidazole-4-carboxamide In a further embodiment, certain novel inventive compounds have the structure shown in Formula (IV) below:

IV wherein $R^1$ and $R^6$ are one or more H, hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkynyl, optionally substituted aliphatic, alicyclic, heteroaliphatic or heterocyclic;

$R^2$ is H, optionally substituted alkyl or cycloalkyl;

$R^3$ and $R^7$ are independently selected from the group consisting of H, $COR^4$, $CONR^4R^5$, $COOR^4$, $SO_2R^4$, optionally substituted alkyl, alkenyl, alkynyl, cyclolalkyl, heterocycloalkyl, aryl or heteroaryl;

$R^4$ and $R^5$ are independently selected from the group consisting of H, OH, NH2, alkyl, alkenyl, alkynyl, cycloalkyl, heterocycloalkyl, aryl, or heteroaryl; and n=0, 1, 2 or 3.

In certain embodiments, $R^1$ is H, Cl or F.
In other embodiments, $R^2$ is H, methyl or ethyl.
In other embodiments, $R^3$ is H.
In other embodiments, $R^4$ and $R^5$ are H, methyl or ethyl.
In other embodiments, $R^6$ is H or F.
In other embodiments $R^7$ is H, methyl, ethyl, propyl, isopropyl, t-butyl, cyclopropyl, cyclobutyl, cyclopentyl, 2-fluorobenzyl or phenylethyl.

Non-limiting examples of compound of formula (IV) include benzyl 3-(4-carbamoyl-1H-benzo[d]imidazol-2-yl)-3,4-dihydroisoquinoline-2(1H)-carboxylate; 2-(1,2,3,4-tetrahydroisoquinolin-3-yl)-1H-benzo[d]imidazole-4-carboxamide; benzyl 3-(4-carbamoyl-1H-benzo[d]imidazol-2-yl)-3-methyl-3,4-dihydroisoquinoline-2(1H)-carboxylate; 2-(3-methyl-1,2,3,4-tetrahydroisoquinolin-3-yl)-1H-benzo[d]imidazole-4-carboxamide; tert-butyl 7-((tert-butoxycarbonyl)amino)-3-(4-carbamoyl-1H-benzo[d]imidazol-2-yl)-3,4-dihydroisoquinoline-2(1H)-carboxylate; tert-butyl 7-amino-3-(4-carbamoyl-1H-benzo[d]imidazol-2-yl)-3,4-dihydroisoquinoline-2(1H)-carboxylate; tert-butyl (3-(4-carbamoyl-1H-benzo[d]imidazol-2-yl)-1,2,3,4-tetrahydroisoquinolin-7-yl)carbamate; and 2-(7-amino-1,2,3,4-tetrahydroisoquinolin-3-yl)-1H-benzo[d]imidazole-4-carboxamide. Other compounds of Formula (IV) include 2-(1,2,3,4,5,6-hexahydrobenzo[c]azocin-3-yl)-1H-benzo[d]imidazole-4-carboxamide; 2-(1,2,3,4,5,6-hexahydrobenzo[d]azocin-2-yl)-1H-benzo[d]imidazole-4-carboxamide; 2-(1,2,3,4,5,6-hexahydrobenzo[d]azocin-4-yl)-1H-benzo[d]imidazole-4-carboxamide; 2-(2,3,4,5-tetrahydro-1H-benzo[c]azepin-3-yl)-1H-benzo[d]imidazole-4-carboxamide; 2-(2,3,4,5-tetrahydro-1H-benzo[d]azepin-2-yl)-1H-benzo[d]imidazole-4-carboxamide; 2-(2-methyl-1,2,3,4,5,6-hexahydrobenzo[d]azocin-2-yl)-1H-benzo[d]imidazole-4-carboxamide; 2-(2-methyl-2,3,4,5-tetrahydro-1H-benzo[d]

azepin-2-yl)-1H-benzo[d]imidazole-4-carboxamide; 2-(3-ethyl-1,2,3,4-tetrahydroisoquinolin-3-yl)-1H-benzo[d]imidazole-4-carboxamide; 2-(3-ethyl-2,3,4,5-tetrahydro-1H-benzo[c]azepin-3-yl)-1H-benzo[d]imidazole-4-carboxamide; 2-(3-methyl-1,2,3,4,5,6-hexahydrobenzo[c]azocin-3-yl)-1H-benzo[d]imidazole-4-carboxamide; 2-(3-methyl-2,3,4,5-tetrahydro-1H-benzo[c]azepin-3-yl)-1H-benzo[d]imidazole-4-carboxamide; 2-(4-ethyl-1,2,3,4,5,6-hexahydrobenzo[d]azocin-4-yl)-1H-benzo[d]imidazole-4-carboxamide; 2-(4-methyl-1,2,3,4,5,6-hexahydrobenzo[d]azocin-4-yl)-1H-benzo[d]imidazole-4-carboxamide; 6-fluoro-2-(1,2,3,4,5,6-hexahydrobenzo[d]azocin-4-yl)-1H-benzo[d]imidazole-4-carboxamide; 6-fluoro-2-(1,2,3,4-tetrahydroisoquinolin-3-yl)-1H-benzo[d]imidazole-4-carboxamide; and 6-fluoro-2-(2,3,4,5-tetrahydro-1H-benzo[c]azepin-3-yl)-1H-benzo[d]imidazole-4-carboxamide.

Additionally, the present invention provides pharmaceutically acceptable derivatives of the inventive compounds, and methods of treating a subject using these compounds, pharmaceutical compositions thereof, or either of these in combination with one or more additional therapeutic agents.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compounds of formulas (I)-(IV) under different conditions and may exist as one or a combination of polymorphs of compounds of general formulas (I)-(IV) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound, followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

As discussed above, this invention provides novel compounds with a range of biological properties. Preferred compounds of this invention have biological activities relevant for the treatment of diseases, conditions or disorders where decrease in PARP activity would be beneficial.

Additionally, the present invention provides pharmaceutically acceptable derivatives of the inventive compounds, and methods of treating a subject using these compounds, pharmaceutical compositions thereof, or either of these in combination with one or more additional therapeutic agents. Certain compounds of the present invention are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. It will be appreciated that the compounds, as described herein, may be substituted with any number of substituents or functional moieties.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

Pharmaceutical Compositions

Accordingly, in another aspect of the present invention, pharmaceutical compositions are provided, which comprise any one or more of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, or it may be any one of a number of agents undergoing approval in the Food and Drug Administration that ultimately obtain approval for the treatment of any disorder related to PARP activity. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

In one aspect, the invention is directed to compositions including pharmaceutical compositions comprising at least one compound of Formulas (I)-(IV).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood, or N-demethylation of a compound of the invention. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The present invention encompasses pharmaceutically acceptable topical formulations of inventive compounds. The term "pharmaceutically acceptable topical formulation", as used herein, means any formulation that is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration-enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Formulations for intraocular administration are also included. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with an anti-inflammatory agent), or they may achieve different effects (e.g., control of any adverse effects). In non-limiting examples, one or more compounds of the invention may be formulated with at least one cytokine, growth factor or other biological, such as an interferon, e.g., alpha interferon, or with at least another small molecule compound. Non-limiting examples of pharmaceutical agents that may be combined therapeutically with compounds of the invention include: antivirals and antifibrotics such as interferon alpha, combination of interferon alpha and ribavirin, Lamivudine, Adefovir dipivoxil and interferon gamma; anticoagulants such as heparin and warfarin; antiplatelets e.g., aspirin, ticlopidine and clopidogrel; other growth factors involved in regeneration, e.g., VEGF and FGF and mimetics of these growth factors; antiapoptotic agents; and motility and morphogenic agents.

In certain embodiments, the pharmaceutical compositions of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and antisickness drugs.

3) Clinical Uses, Pharmaceutical Uses and Methods of Treatment

Clinical Uses of the Compounds of the Invention

As described herein, the invention provides methods for the use of any of the compounds disclosed herein for treating or lessening the severity of a disease, disorder or condition associated with PARP activity, and where inhibition of such activity is beneficial for the treatment, lessening the severity of or preventing the occurrence or relapse thereof. Such diseases, disorders and conditions include, but are not limited to, muscular dystrophy, hepatic ischemia-reperfusion injury, pancreatitis, cerebral infarction, ischemic heart disease, damaged and/or ischemic organs, transplants or grafts; ischemia/reperfusion injury; stroke, traumatic head injury, spinal cord injury, and other cerebrovascular diseases; myocardial ischemia; atherosclerosis; peripheral vascular disease; other cardiovascular diseases; diabetes; renal failure; multiple sclerosis; and neurodegenerative diseases such as Parkinsonism and Alzheimer disease. In certain exemplary embodiments, the method is for the treatment of wounds for acceleration of healing; amelioration of ischemia/reperfusion injury in the brain, heart, liver, kidney, or other tissues or organs; normalization of myocardial perfusion as a consequence of chronic cardiac ischemia or myocardial infarction; renal failure secondary to chronic diabetes and/or hypertension; and/or diabetes mellitus. Use of the compound is also provided for prophylaxis or preventing the occurrence of the diseases in subjects, and in particular subjects susceptible to of exhibiting risk factors for, the aforementioned diseases and conditions.

Furthermore, compounds embodied herein are also useful for the treatment of various dysproliferative diseases including but not limited to dysproliferative diseases such as cancer, as well as inflammatory disease in particular where inflammation, especially chronic inflammation, leads to inappropriate vascularization. Examples of cancers, tumors, malignancies, neoplasms, and other dysproliferative diseases that can be treated according to the invention include leukemias, such as myeloid and lymphocytic leukemias, lymphomas, myeloproliferative diseases, and solid tumors, such as but not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. In preferred but non-limiting embodiments, brain tumors, including glioma, and pancreatic cancers are amenable to treatment by the compounds of the present invention.

The invention also provides methods for the use of any of the compounds disclosed herein for use as adjuvant therapy with DNA-damaging chemotherapeutics for treatment of various forms of cancer including but not limited melanoma, breast, ovarian and glioblastoma and in treatment of HIV infection. Use of the compound is also provided for prophylaxis or preventing the occurrence of the diseases in subjects, and in particular subjects susceptible to of exhibiting risk factors for, the aforementioned diseases and conditions.

The invention also provides methods for the use of any of the compounds disclosed herein for use as adjuvant therapy with DNA-damaging chemotherapeutics for treatment of various forms of cancer including but not limited melanoma, breast, ovarian and glioblastoma and in treatment of HIV infection. Use of the compound is also provided for prophylaxis or preventing the occurrence of the diseases in subjects, and in particular subjects susceptible to of exhibiting risk factors for, the aforementioned diseases and conditions.

Examples of inflammatory diseases toward which compounds of the invention have benefit include rheumatoid arthritis, atherosclerosis, and neovascularization in the eye as a consequence of diabetic retinopathy. Compounds embodied herein are also useful for potentiating the activity of compounds for the treatment of the aforementioned diseases, in particular chemotherapeutic agents.

The present invention is also directed to treatment of non-malignant tumors and other disorders involving inappropriate cell or tissue growth by administering a therapeutically effective amount of an agent of the invention. For example, the invention is useful for the treatment of arteriovenous (AV) malformations, particularly in intracranial sites. The invention can also be used to treat psoriasis, a dermatologic condition that is characterized by inflammation and vascular proliferation; benign prostatic hypertrophy, a condition associated with inflammation and possibly vascular proliferation; and cutaneous fungal infections. Treatment of other hyperproliferative disorders is also embraced herein. The agents may also be used topically to remove warts, birthmarks, moles, nevi, skin tags, lipomas, angiomas including hemangiomas, and other cutaneous lesions for cosmetic or other purposes.

In another embodiment, a method is provided that comprises the step of administering to a subject suffering from a disease or condition associated with PARP activity an effective amount of a compound of any one of formulas (I)-(IV) or a composition thereof; wherein the compound is characterized by its ability to inhibit PARP activity. In a further embodiment, the disease or condition can be muscular dystrophy, hepatic ischemia-reperfusion injury, cerebral infarction, ischemic heart disease, damaged and/or ischemic organs, transplants or grafts; ischemia/reperfusion injury; stroke, traumatic head injury, spinal cord injury, and other cerebrovascular diseases; myocardial ischemia; atherosclerosis; peripheral vascular disease; other cardiovascular diseases; diabetes; renal failure; multiple sclerosis; and neurodegenerative diseases such as Parkinsonism and Alzheimer disease. In certain exemplary embodiments, the method is for the treatment of wounds for acceleration of healing; amelioration of ischemia/reperfusion injury in the brain, heart, liver, kidney, or other tissues or organs; normalization of myocardial perfusion as a consequence of chronic cardiac ischemia or myocardial infarction; renal failure secondary to chronic diabetes and/or hypertension; and/or diabetes mellitus. In other embodiments the disease or condition is a dysproliferative disease such as cancer. In another embodiment the disease is an inflammatory disease. In another embodiment, the compound inhibits PARP with an in vitro $IC_{50}$ of about 1 to about 5 micromolar. In another embodiment, the compound inhibits PARP with an in vitro $IC_{50}$ of about 0.1 to about 1 micromolar. In another embodiment, the compound inhibits PARP with an in vitro $IC_{50}$ of about 0.001 to about 0.1 micromolar. In another embodiment, the compound inhibits PARP with an in vitro $IC_{50}$ of more than about 0.001 micromolar. In another embodiment, the compound inhibits PARP with an in vitro $IC_{50}$ of less than about 0.001 micromolar.

Exemplary Assays

Efficacy of the compounds of the invention on the aforementioned disorders and diseases or the potential to be of benefit for the prophylaxis or treatment thereof may be demonstrated in various studies, ranging from biochemical effects evaluated in vitro and effects on cells in culture, to in-vivo models of disease, wherein direct clinical manifestations of the disease can be observed and measured, or wherein early structural and/or functional events occur that are established to be involved in the initiation or progression of the disease. The positive effects of the compounds of the invention have been demonstrated in a variety of such assays and models, for a number of diseases and disorders. One skilled in the art can readily determine following the guidance described herein that a compound of the invention is an inhibitor of PARP.

As detailed in the exemplification herein, in assays to determine the ability of compounds to inhibit PARP and protect against apoptosis and necrosis among the other beneficial activities thereof, certain inventive compounds exhibited $ED_{50}$ values $\leq 50$ μM. In certain other embodiments, inventive compounds exhibit $ED_{50}$ values $\leq 40$ μM. In certain other embodiments, inventive compounds exhibit $ED_{50}$ values $\leq 30$ μM. In certain other embodiments, inventive compounds exhibit $ED_{50}$ values $\leq 20$ μM. In certain other embodiments, inventive compounds exhibit $ED_{50}$ values $\leq 10$ μM. In certain other embodiments, inventive compounds exhibit $ED_{50}$ values $\leq 7.5$ μM. In certain embodiments, inventive compounds exhibit $ED_{50}$ values $\leq 5$ μM. In certain other embodiments, inventive compounds exhibit $ED_{50}$ values $\leq 2.5$ μM. In certain embodiments, inventive compounds exhibit $ED_{50}$ values $\leq 1$ μM. In certain other embodiments, inventive compounds exhibit $ED_{50}$ values $\leq 750$ nM. In certain other embodiments, inventive compounds exhibit $ED_{50}$ values $\leq 500$ nM. In certain other embodiments, inventive compounds exhibit $ED_{50}$ values $\leq 250$ nM. In certain other embodiments, inventive compounds exhibit $ED_{50}$ values≦100 nM. In other embodiments, exemplary compounds exhibited $ED_{50}$ values≦75 nM. In other embodiments, exemplary compounds exhibited $ED_{50}$ values≦50 nM. In other embodiments, exemplary compounds exhibited $ED_{50}$ values≦40 nM. In other embodiments, exemplary compounds exhibited $ED_{50}$ values≦30 nM. In other embodiments, exemplary compounds exhibited $ED_{50}$ values≦20 nM. In other embodiments, exemplary compounds exhibited $ED_{50}$ values≦10 nM. In other embodiments, exemplary compounds exhibited $ED_{50}$ values≦5 nM. In other embodiments, exemplary compounds exhibited $ED_{50}$ values≦1 nM.

Furthermore, in assays to determine the ability of compounds to inhibit PARP, some inventive compounds exhibited $IC_{50}$ values>5 µM. In certain other embodiments, inventive compounds exhibit $IC_{50}$ values≦5 µM. In certain other embodiments, inventive compounds exhibit $IC_{50}$ values≦1 µM. In certain other embodiments, inventive compounds exhibit $IC_{50}$ values≦0.3 µM. In certain other embodiments, inventive compounds exhibit $IC_{50}$ values≦0.1 µM. In certain other embodiments, inventive compounds exhibit $IC_{50}$ values≦0.03 µM. In certain embodiments, inventive compounds exhibit $IC_{50}$ values≦0.01 µM. In certain other embodiments, inventive compounds exhibit $IC_{50}$ values≦0.003 µM. In certain embodiments, inventive compounds exhibit $IC_{50}$ values≦0.001 µM.

Pharmaceutical Uses and Methods of Treatment

Methods are provided herein for the treatment any disorder wherein inhibition of PARP activity is desirable, comprising administering a therapeutically effective amount of a compound of the invention as described herein, to a subject in need thereof. In certain embodiments, a method for the treatment disorders related to these activities is provided comprising administering a therapeutically effective amount of an inventive compound, or a pharmaceutical composition comprising an inventive compound to a subject in need thereof, in such amounts and for such time as is necessary to achieve the desired result.

In certain embodiments, the method involves the administration of a therapeutically effective amount of the compound or a pharmaceutically acceptable derivative thereof to a subject (including, but not limited to a human or animal) in need of it. Subjects for which the benefits of the compounds of the invention are intended for administration include, in addition to humans, livestock, domesticated, zoo and companion animals.

As discussed above this invention provides novel compounds that have the beneficial activities described herein. In certain embodiments, the inventive compounds are useful for the treatment of renal ischemia and ischemia of other organs. In other embodiments, compounds embodied herein are useful for the treatment of cancer and other dysproliferative diseases and disorders.

It will be appreciated that the compounds and compositions, according to the method of the present invention, may be administered using any amount and any route of administration effective for the treatment of the conditions or diseases in which inhibiting PARP has a therapeutically useful role. Thus, the expression "effective amount" as used herein, refers to a sufficient amount of agent to exhibit this activity and to exhibit a therapeutic effect. The exact amount required will vary from subject to subject, depending on the species, age, and general condition of the subject, the severity of the disease, the particular therapeutic agent, its mode and/or route of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, subcutaneously, intradermally, intra-ocularly, topically (as by powders, ointments, or drops), buccally, as an oral or nasal spray, or the like, depending on the severity of the disease or disorder being treated. In certain embodiments, the compounds of the invention may be administered at dosage levels of about 0.001 mg/kg to about 50 mg/kg, preferably from about 0.1 mg/kg to about 10 mg/kg for parenteral administration, or preferably from about 1 mg/kg to about 50 mg/kg, more preferably from about 10 mg/kg to about 50 mg/kg for oral administration, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Moreover, pharmaceutical compositions comprising one or more compounds of the invention may also contain other compounds or agents for which co-administration with the compound(s) of the invention is therapeutically advantageous. As noted above, embodied compounds potentiate the chemotherapeutic activity of anticancer agents. As many pharmaceutical agents are used in the treatment of the diseases and disorders for which the compounds of the invention are also beneficial, any may be formulated together for administration. Synergistic formulations are also embraced herein, where the combination of at least one compound of the invention and at least one other compounds act more beneficially than when each is given alone. Non-limiting examples of pharmaceutical agents that may be combined therapeutically with compounds of the invention include anti-cancer agents such as, aldesleukin (PROLEUKIN); alemtuzumab (CAMPATH); alitretinoin (PANRETIN); allopurinol (ZYLOPRIM); altretamine (HEXALEN); amifostine (ETHYOL); anastrozole (ARIMIDEX); arsenic trioxide (TRISENOX); asparaginase (ELSPAR); BCG Live (TICE BCG); bexarotene capsules or gel (TARGRETIN); bleomycin (BLENOXANE); busulfan intravenous (BUSULFEX); busulfan oral (MYLERAN); calusterone (METHOSARB); capecitabine (XELODA); carboplatin (PARAPLATIN); carmustine (BCNU, BICNU); carmustine with Polifeprosan 20 Implant (GLIADEL WAFER); celecoxib (CELEBREX); chlorambucil (LEUKERAN); cisplatin (PLATINOL); cladribine (LEUSTATIN, 2-CDA); cyclophosphamide (CYTOXAN, NEOSAR); cytarabine (CYTOSAR-U); cytarabine liposomal (DEPOCYT); dacarbazine (DTIC-DOME); dactinomycin, actinomycin D (COSMEGEN); darbepoetin alfa (ARANESP); daunorubicin liposomal (DANUOXOME); daunorubicin, daunomycin (DAUNORUBICIN or CERUBIDINE); denileukin diftitox (ONTAK); dexrazoxane (ZINECARD); docetaxel (TAXOTERE); doxorubicin (ADRIAMYCIN, RUBEX); doxorubicin liposomal (DOXIL); dromostanolone propionate (DROMOSTANOLONE or MASTERONE INJECTION); Elliott's B solution (ELLIOTT'S B SOLUTION); epirubicin (ELLENCE); Epoetin alfa (EPOGEN); estramustine (EMCYT); etoposide phosphate (ETOPOPHOS); etoposide, VP-16 (VEPESID); exemestane (AROMASIN); filgrastim (NEUPOGEN); floxuridine (intraarterial) (FUDR); fludarabine (FLUDARA); fluorouracil, 5-FU (ADRUCIL); fulvestrant (FASLODEX); gemcitabine (GEMZAR); gemtuzumab ozogamicin (MYLOTARG); goserelin acetate (ZOLADEX); hydroxyurea (HYDREA); ibritumomab Tiuxetan (ZEVALIN); idarubicin (IDAMYCIN); ifosfamide (IFEX); interferon alfa-2a (ROFERON-A or INTRON A); irinotecan (CAMPTOSAR); letrozole (FEMARA); leucovorin (WELLCOVORIN or LEUCOVORIN); levamisole (ERGAMISOL); lomustine, CCNU (CEEBU); meclorethamine, nitrogen mustard (MUSTARGEN); megestrol acetate (MEGACE); melphalan, L-PAM (ALKERAN); mercaptopurine, 6-MP (PURINETHOL); mesna (MESNEX); methotrexate (METHOTREXATE); methoxsalen (UVADEX); mitomycin C (MUTAMYCIN or MITOZYTREX); mitotane (LYSODREN); mitoxantrone (NOVANTRONE); nandrolone phenpropionate (DURABOLIN-50); nofetumomab (VERLUMA); oprelvekin (NEUMEGA); oxaliplatin (ELOXATIN); paclitaxel (PAXENE or TAXOL); pamidronate (AREDIA); pegademase (ADAGEN; PEGADEMASE BOVINE); pegaspargase (ONCASPAR); pegfilgrastim (NEULASTA); pentostatin (NIPENT); pipobroman (VERCYTE); plicamycin, mithramycin (MITHRACIN); porfimer sodium (PHOTOFRIN); procarbazine (MATULANE); quinacrine (ATABRINE); rasburicase (ELITEK); rituximab (RITUXAN); sargramostim (PROKINE); streptozocin (ZANOSAR); talc (SCLEROSOL); tamoxifen (NOLVADEX); temozolomide (TEMODAR); teniposide, VM-26 (VUMON); testolactone (TESLAC); thioguanine, 6-TG (THIOGUANINE); thiotepa (THIOPLEX); topotecan (HYCAMTIN); toremifene (FARESTON); tositumomab (BEXXAR); trastuzumab (HERCEPTIN); tretinoin, ATRA (VESANOID); uracil mustard (URACIL MUSTARD CAPSULES); valrubicin (VALSTAR); vinblastine (VELBAN); vincristine (ONCOVIN); vinorelbine (NAVELBINE); and zoledronate (ZOMETA).

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a well-established literature of small molecule chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium or sodium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica or preparative TLC on silica, using a single solvent or mixed solvent as eluent. Suitably purified desired product containing elutes were combined and concentrated under reduced pressure at an appropriate temperature (generally less than 45° C.) to constant mass.

Synthesis of Exemplary Compounds:

Example 1

Benzyl 3-(4-carbamoyl-1H-benzo[d]imidazol-2-yl)-3,4-dihydroisoquinoline-2-(1H)-carboxylate Step-1: To a solution of 2-((benzyloxy)carbonyl)-1,2,3,4-tetrahydroisoquinoline-3-carboxylic acid (1.0 g, 3.21 mmol) in anhydrous DMF (20 ml) was added EDC.HCl (1.85 g, 9.63 mmol), HOBt (681 mg, 5.05 mmol) and triethylamine (0.7 ml, 4.81 mmol) and the mixture was stirred at RT for 10 min. To this reaction mixture, 2,3-diaminobenzamide (606 mg, 4.01 mmol) was added and was stirred at RT over night. The reaction was poured in to water, stirred for 30 min and extracted with ethyl acetate. The organic layer was washed with brine and dried over anhydrous sodium sulfate and concentrated under vacuum to yield benzyl 3-(2-amino-3-carbomoylphenylcarbamoyl)-3,4-dihydroisoquinoline-2(1H)-carboxylate. MS (ES+): m/z 445.1 [M+H]$^+$ Step-2: A solution of benzyl 3-(2-amino-3-carbomoylphenylcarbamoyl)-3,4-dihydroisoquinoline-2(1H)-carboxylate (1.3 g, 2.92 mmol) in acetic acid (20 ml) was heated to 80° C. and stirred overnight. The reaction mixture was concentrated, neutralized with aq. NaHCO$_3$ and extracted with DCM. The DCM layer was washed with brine, dried over anhydrous sodium sulfate and evaporated. Purification of the crude product over silica gel column using methanol/dichloromethane (1:10) mixture as eluent afforded benzyl 3-(4-carbamoyl-1H-benzo[d]imidazol-2-yl)-3,4-dihydroisoquinoline-2-(1H)-carboxylate. MS (ES+): m/z 427.1 [M+H]$^+$ Example 2

2-(1,2,3,4-Tetrahydroisoquinolin-3-yl)-1H-benzo[d]imidazole-4-carboxamide

To a solution of benzyl 3-(4-carbamoyl-1H-benzo[d]imidazol-2-yl)-3,4-dihydroisoquinoline-2-(1H)-carboxylate (400 mg, 0.938 mmol) in methanol (20 ml) was added 10% Pd/C (40 mg) and the reaction mixture was degassed and stirred under H$_2$ at 1 atmosphere pressure for 2 h at RT. The reaction mixture was filtered and the filtrate was concentrated and the crude was product further triturated with ether to afford 2-(1,2,3,4-tetrahydroisoquinolin-3-yl)-1H-benzo[d]imidazole-4-carboxamide. MS (ES+): m/z 293.1 [M+H]$^+$ Example 3

Benzyl 2-(4-carbamoyl-1H-benzo[d]imidazol-2-yl)indoline-1-carboxylate

Step-1: To a solution of 1-((benzyloxy)carbonyl)indoline-2-carboxylic acid (1.0 g, 3.37 mmol) in anhydrous DMF (20 ml) was added EDC.HCl (1.93 g, 10.10 mmol), HOBt (681 mg, 5.05 mmol) and triethylamine (0.7 ml, 5.05 mmol) at RT and the mixture was stirred for 10 min. To this reaction mixture, 2,3-diaminobenzamide (635 mg, 4.20 mmol) was added and heated to 80° C. over night. The reaction mixture was poured into ice cold water and stirred for 30 min. The precipitate formed was filtered and dried under vacuum to yield benzyl 2-(2-amino-3-carbamoylphenylcarbamoyl)indoline-1-carboxylate. MS (ES+): m/z 431.1 [M+H]$^+$ Step-2: A solution of benzyl 2-(2-amino-3-carbamoylphenylcarbamoyl) indoline-1-carboxylate (1.5 g, 3.48 mmol) in acetic acid (20 ml) was heated to 80° C. and stirred overnight. The reaction mixture was concentrated, neutralized with aq.

NaHCO₃ and extracted with DCM. The DCM layer was washed with brine, dried over anhydrous sodium sulfate and evaporated. Purification of the crude product over silica gel column using methanol/dichloromethane (1:10) mixture as eluent afforded benzyl 2-(4-carbamoyl-1H-benzo[d]imidazol-2-yl)indoline-1-carboxylate. MS (ES+): m/z 413.1 [M+H]⁺

Example 4

2-(Indolin-2yl)-1H-benzo[d]imidazole-4-carboxamide

To a solution of benzyl 2-(4-carbamoyl-1H-benzo[d]imidazol-2-yl)indoline-1-carboxylate (800 mg, 1.94 mmol) in ethyl acetate (50 ml) was added 10% Pd/C (80 mg) and the reaction mixture was degassed and stirred under H₂ at 1 atmospheric pressure for 2 h at RT. The reaction mixture was filtered, the filtrate concentrated and the crude product was further triturated with ether to afford 2-(indolin-2-yl)-1H-benzo[d]imidazole-4-carboxamide. MS (ES+): m/z 279.1 [M+H]⁺

Example 5

Benzyl 1-(4-carbamoyl-1H-benzo[d]imidazol-2-yl)-3,4-dihydroisoquinoline-2(1H)-carboxylate Step-1: To a solution of 2-((benzyloxy)carbonyl)-1,2,3,4-tetrahydroisoquinoline-1-carboxylic acid (560 mg, 1.8 mmol) in anhydrous DMF (7 ml) was added EDC.HCl (1.035 g, 5.4 mmol), HOAt (367 mg, 2.7 mmol) and triethylamine (0.375 ml, 2.7 mmol) at RT and the mixture was stirred for 10 min. To this reaction mixture, 2,3-diaminobenzamide (302 mg, 2 mmol) was added and heated to 55° C. over night. The reaction mixture was poured into ice cold water and stirred for 30 min. The precipitate formed was filtered and dried under vacuum to yield benzyl 1-((2-amino-3-carbamoylphenyl)carbamoyl)-3,4-dihydroisoquinoline-2(1H)-carboxylate. MS (ES+): m/z 445.22 [M+H]⁺

Step-2: A solution of benzyl 1-((2-amino-3-carbamoylphenyl)carbamoyl)-3,4-dihydroisoquinoline-2(1H)-carboxylate (425 mg, 0.956 mmol) in acetic acid (5 ml) was heated to 80° C. and stirred overnight. The reaction mixture was concentrated, neutralized with aq. NaHCO₃ and extracted with DCM. The DCM layer was washed with brine, dried over anhydrous sodium sulfate and evaporated. Purification of the crude product over silica gel column using ethyl acetate/hexane mixture (1:1) as eluent afforded benzyl 1-(4-carbamoyl-1H-benzo[d]imidazol-2-yl)-3,4-dihydroisoquinoline-2(1H)-carboxylate. MS (ES+): m/z 427.2 [M+H]⁺

Example 6

2-(1,2,3,4-Tetrahydroisoquinolin-1-yl)-1H-benzo[d]imidazole-4-carboxamide

Following the procedure described above for example 2, benzyl 1-(4-carbamoyl-1H-benzo[d]imidazol-2-yl)-3,4-dihydroisoquinoline-2(1H)-carboxylate was converted to 2-(1,2,3,4-tetrahydroisoquinolin-1-yl)-1H-benzo[d]imidazole-4-carboxamide. MS (ES+): m/z 293.15 [M+H]⁺

Example 7

Benzyl 1-(4-carbamoyl-1H-benzo[d]imidazol-2-yl)isoindoline-2-carboxylate

Following the procedure described above for example 3, 2-((benzyloxy)carbonyl)isoindoline-1-carboxylic acid was converted to benzyl 1-(4-carbamoyl-1H-benzo[d]imidazol-2-yl)isoindoline-2-carboxylate. MS (ES+): m/z 413.30 [M+H]⁺

Example 8

2-(Isoindolin-1-yl)-1H-benzo[d]imidazole-4-carboxamide

Following the procedure described above for example 4, benzyl 1-(4-carbamoyl-1H-benzo[d]imidazol-2-yl)isoindoline-2-carboxylate was converted to 2-(isoindolin-1-yl)-1H-benzo[d]imidazole-4-carboxamide. MS (ES+): m/z 279.1 [M+H]⁺

Example 9 tert-Butyl 2-(4-carbamoyl-1H-benzo[d]imidazol-2-yl)-3,4-dihydroquinoline-1(2H)-carboxylate Step-1: To a solution of 1-(tert-butoxycarbonyl)-1,2,3,4-tetrahydroquinoline-2-carboxylic acid (100 mg, 0.36 mmol) in anhydrous DMF (3 ml) was added EDC.HCl (207 mg, 1.08 mmol), HOBt (73.4 mg, 0.54 mmol) and triethylamine (0.08 ml, 0.54 mmol) at RT and the mixture was stirred for 10 min. To this reaction mixture, 2,3-diaminobenzamide (60 mg, 0.4 mmol) was added and heated to 55° C. over night. The reaction mixture was poured into ice cold water and stirred for 30 min. The precipitate formed was filtered and dried under vacuum to yield benzyl 2-((2-amino-3-carbamoylphenyl)carbamoyl)-3,4-dihydroquinoline-1(2H)-carboxylate. MS (ES+): m/z 2411.30 [M+H]⁺

Step-2: A solution of benzyl 2-((2-amino-3-carbamoylphenyl)carbamoyl)-3,4-dihydroquinoline-1(2H)-carboxylate (50 mg, 0.122 mmol) in acetic acid (2 ml) was heated to 80° C. and stirred for 2 h. The reaction mixture was concentrated, neutralized with aq. NaHCO₃ and extracted with DCM. The DCM layer was washed with brine, dried over anhydrous sodium sulfate and evaporated. Purification of the crude product over preparative TLC using ethyl acetate/hexane mixture (2:1) as eluent afforded tert-butyl 2-(4-carbamoyl-1H-benzo[d]imidazol-2-yl)-3,4-dihydroquinoline-1(2H)-carboxylate. MS (ES+): m/z 393.23 [M+H]⁺

Example 10

2-(1,2,3,4-Tetrahydroquinolin-2-yl)-1H-benzo[d]imidazole-4-carboxamide

A mixture of tert-butyl 2-(4-carbamoyl-1H-benzo[d]imidazol-2-yl)-3,4-dihydroquinoline-1(2H)-carboxylate (17 mg, 0.043 mmol) and HCl in methanol (1.25 M, 1 mL) was stirred at 40° C. overnight. Methanol was removed under reduced pressure, aq. sodium bicarbonate solution was added and extracted with DCM. The DCM layer was washed with brine, dried over anhydrous sodium sulfate and evaporated to afford 2-(1,2,3,4-Tetrahydroquinolin-2-yl)-1H-benzo[d]imidazole-4-carboxamide. MS (ES+): m/z 315.13 [M+Na]⁺

Example 11

Benzyl 3-(4-carbamoyl-1H-benzo[d]imidazol-2-yl)-3-methyl-3,4-dihydroisoquinoline-2(1H)-carboxylate Step-1: A mixture of 2-((benzyloxy)carbonyl)-1,2,3,4-tetrahydroisoquinoline-3-carboxylic acid (2 g, 6.42 mmol) and conc. sulfuric acid (0.45 mL) in methanol was refluxed overnight. The reaction mixture was concentrated, neutralized with aq. sodium bicarbonate and extracted with DCM. The DCM layer was washed with brine, dried over anhydrous sodium sulfate and evaporated to afford 2-benzyl 3-methyl 3,4-dihydroisoquinoline-2,3(1H)-dicarboxylate. MS (ES+): m/z 348.12 [M+Na]$^+$ Step-2: To a solution of 2-benzyl 3-methyl 3,4-dihydroisoquinoline-2,3(1H)-dicarboxylate (3 g, 9.23 mmol) in THF (30 mL) at −80° C. was added sodium hexamethyldisilazane (1M, 23.1 mL, 23.1 mmol) and stirred for 20 min. Methyl iodide (1.44 mL, 23.1 mmol) was added and the reaction was allowed to warm to −20° C. and stirred at −20° C. for 6 h. The reaction was quenched with water, neutralized with 2N HCl and extracted with ethyl acetate. The organic layer was washed with brine, dried over anhydrous sodium sulfate and evaporated to afford 2-benzyl 3-methyl 3-methyl-3,4-dihydroisoquinoline-2,3(1H)-dicarboxylate. MS (ES+): m/z 340.20 [M+H]$^+$ Step-3: To a solution of 2-benzyl 3-methyl 3-methyl-3,4-dihydroisoquinoline-2,3(1H)-dicarboxylate in THF (1.2 mL) was added lithium hydroxide (50.5 mg, 1.204 mmol) in water (0.6 mL). Methanol (0.72 mL) was added till homogeneous solution was obtained and the reaction was heated at 60° C. overnight. The reaction was concentrated, acidified to pH 2 using 2 N HCl, extracted with ethyl acetate. The organic layer was washed with brine, dried over anhydrous sodium sulfate and evaporated to afford the crude product which was purified by preparative TLC using hexane/ethyl acetate mixture (1:1) to afford 2-((benzyloxy)carbonyl)-3-methyl-1,2,3,4-tetrahydroisoquinoline-3-carboxylic acid. MS (ES+): m/z 326.15 [M+H]$^+$ Step-4: To a solution of 2-((benzyloxy)carbonyl)-3-methyl-1,2,3,4-tetrahydroisoquinoline-3-carboxylic acid (620 mg, 1.91 mmol) in anhydrous DMF (5 ml) was added EDC.HCl (1.098 mg, 5.73 mmol), HOAt (390 mg, 2.87 mmol) and triethylamine (0.4 ml, 2.87 mmol) at RT and the mixture was stirred for 10 min. To this reaction mixture, 2,3-diaminobenzamide (346 mg, 2.29 mmol) was added and heated to 55° C. for 3 days. The reaction mixture was poured into ice cold water and stirred for 30 min. The precipitate formed was filtered and dried under vacuum and purified by preparative TLC using ethyl acetate as eluent to afford benzyl 3-((2-amino-3-carbamoylphenyl)carbamoyl)-3-methyl-3,4-dihydroisoquinoline-2(1H)-carboxylate. MS (ES+): m/z 481.2 [M+Na]$^+$ Step-5: A solution of benzyl 3-((2-amino-3-carbamoylphenyl)carbamoyl)-3-methyl-3,4-dihydroisoquinoline-2(1H)-carboxylate (40 mg, 0.087 mmol) in acetic acid (2 ml) was heated to 80° C. and stirred overnight. The reaction was further heated to 120° C. for 3 h. The reaction mixture was concentrated, neutralized with aq. NaHCO$_3$ and extracted with ethyl acetate. The ethyl acetate layer was washed with brine, dried over anhydrous sodium sulfate and evaporated. Purification of the crude product by preparative TLC using hexane/ethyl acetate (1:1) mixture as eluent afforded benzyl 3-(4-carbamoyl-1H-benzo[d]imidazol-2-yl)-3-methyl-3,4-dihydroisoquinoline-2(1H)-carboxylate. MS (ES+): m/z 441.22 [M+H]$^+$ Example 12

2-(3-Methyl-1,2,3,4-tetrahydroisoquinolin-3-yl)-1H-benzo[d]imidazole-4-carboxamide Following the procedure described above for example 2, benzyl 3-(4-carbamoyl-1H-benzo[d]imidazol-2-yl)-3-methyl-3,4-dihydroisoquinoline-2(1H)-carboxylate was converted to 2-(3-methyl-1,2,3,4-tetrahydroisoquinolin-3-yl)-1H-benzo[d]imidazole-4-carboxamide. MS (ES+): m/z 329.16 [M+Na]+

Example 13 tert-Butyl 7-((tert-butoxycarbonyl)amino)-3-(4-carbamoyl-1H-benzo[d]imidazol-2-yl)-3,4-dihydroisoquinoline-2(1H)-carboxylate Step-1: To a mixture of 7-amino-2-(tert-butoxycarbonyl)-1,2,3,4-tetrahydroisoquinoline-3-carboxylic acid (300 mg, 1.03 mmol) in 10% aq. acetic acid (8 mL) was added di(tert-butyl)dicarbonate (236 mg, 1.08 mmol) in 1,4-dioxane (8 mL) and the mixture was stirred for 4 h at RT. The reaction mixture was diluted with DCM and basified to pH 8 and extracted with DCM. The DCM extract was dried over anhydrous sodium sulfate and evaporated. The crude product was purified by preparative TLC using 10% methanol in DCM as eluent to afford 2-(tert-butoxycarbonyl)-7-((tert-butoxycarbonyl)amino)-1,2,3,4-tetrahydroisoquinoline-3-carboxylic acid. MS (ES+): m/z 451.21 [M+Na]$^+$ Step-2: To a solution of 2-(tert-butoxycarbonyl)-7-((tert-butoxycarbonyl)amino)-1,2,3,4-tetrahydroisoquinoline-3-carboxylic acid (200 mg, 0.51 mmol) in anhydrous DMF (3 mL) was added EDC.HCl (293 mg, 1.53 mmol), HOAt (105 mg, 0.77 mmol) and triethylamine (0.107 ml, 0.77 mmol) at RT and the mixture was stirred for 10 min. To this reaction mixture, 2,3-diaminobenzamide (77 mg, 0.51 mmol) was added and heated to 80° C. over night. The reaction mixture was concentrated and purified by preparative TLC to afford tert-butyl 3-((2-amino-3-carbamoylphenyl)carbamoyl)-7-((tert-butoxycarbonyl)amino)-3,4-dihydroisoquinoline-2(1H)-carboxylate. MS (ES+): m/z 526.30 [M+H]$^+$ Step-3: A solution of tert-butyl 3-((2-amino-3-carbamoylphenyl)carbamoyl)-7-((tert-butoxycarbonyl)amino)-3,4-dihydroisoquinoline-2(1H)-carboxylate (70 mg, 0.133 mmol) in acetic acid (2 ml) was heated to 80° C. and stirred for 2.5 h. The reaction mixture was concentrated, neutralized with aq. NaHCO$_3$ and extracted with DCM. The DCM layer was washed with brine, dried over anhydrous sodium sulfate and evaporated. Purification of the crude product by preparative TLC using methanol/dichloromethane (1:15) mixture as eluent afforded tert-butyl 7-((tert-butoxycarbonyl)amino)-3-(4-carbamoyl-1H-benzo[d]imidazol-2-yl)-3,4-dihydroisoquinoline-2(1H)-carboxylate. MS (ES+): m/z 508.28 [M+H]$^+$ Example 14 tert-Butyl 7-amino-3-(4-carbamoyl-1H-benzo[d]imidazol-2-yl)-3,4-dihydroisoquinoline-2(1H)-carboxylate Example 15 tert-Butyl (3-(4-carbamoyl-1H-benzo[d]imidazol-2-yl)-1,2,3,4-tetrahydroisoquinolin-7-yl)carbamates; and Example 16

2-(7-Amino-1,2,3,4-tetrahydroisoquinolin-3-yl)-1H-benzo[d]imidazole-4-carboxamide A mixture of tert-butyl 7-((tert-butoxycarbonyl)amino)-3-(4-carbamoyl-1H-benzo[d]imidazol-2-yl)-3,4-dihydroisoquinoline-2(1H)-carboxylate (10 mg, 0.0197 mmol) and HCl in methanol (1.25 M, 1 mL) was stirred at 40° C. for 8 h.

Methanol was removed under reduced pressure, aq. sodium bicarbonate solution was added and extracted with 10% methanol in DCM. The organic layer was washed with brine, dried over anhydrous sodium sulfate and evaporated. Purification of the crude product by preparative TLC using methanol/dichloromethane (1:10) mixture containing 1% of 7N ammonia in methanol as eluent afforded the following three compounds. tert-Butyl 7-amino-3-(4-carbamoyl-1H-benzo[d]imidazol-2-yl)-3,4-dihydroisoquinoline-2(1H)-carboxylate. MS (ES+): m/z 408.23 [M+H]$^+$; tert-Butyl (3-(4-carbamoyl-1H-benzo[d]imidazol-2-yl)-1,2,3,4-tetrahydroisoquinolin-7-yl)carbamate. MS (ES+): m/z 408.23 [M+H]$^+$; 2-(7-Amino-1,2,3,4-tetrahydroisoquinolin-3-yl)-1H-benzo[d]imidazole-4-carboxamide. MS (ES+): m/z 330.15 [M+H]$^+$ Furthermore, the following additional, exemplary and non-limiting compounds can be made using appropriate starting materials and following the guidance portrayed in the synthetic procedures described above: 2-(1,2,3,4,5,6-hexahydrobenzo[b]azocin-2-yl)-1,4-benzo[d]imidazole-4-carboxamide; 2-(2,3,4,5-tetrahydro-1H-benzo[b]azepin-2-yl)-1H-benzo[d]imidazole-4-carboxamide; 2-(2-ethylindolin-2-yl)-1H-benzo[d]imidazole-4-carboxamide; 2-(2-methyl-1,2,3,4-tetrahydroquinolin-2-yl)-1H-benzo[d]imidazole-4-carboxamide; 2-(2-methyl-2,3,4,5-tetrahydro-1H-benzo[b]azepin-2-yl)-1H-benzo[d]imidazole-4-carboxamide; 2-(2-methylindolin-2-yl)-1H-benzo[d]imidazole-4-carboxamide; 6-fluoro-2-(indolin-2-yl)-1H-benzo[d]imidazole-4-carboxamide; 2-(2-methyl-1,2,3,4,5,6-hexahydrobenzo[b]azocin-2-yl)-1H-benzo[d]imidazole-4-carboxamide; 2-(1,2,3,4,5,6-hexahydrobenzo[c]azocin-1-yl)-1H-benzo[d]imidazole-4-carboxamide; 2-(1-methyl-1,2,3,4,5,6-hexahydrobenzo[c]azocin-1-yl)-1H-benzo[d]imidazole-4-carboxamide; 2-(1-methyl-1,2,3,4-tetrahydroisoquinolin-1-yl)-1H-benzo[d]imidazole-4-carboxamide; 2-(1-methyl-2,3,4,5-tetrahydro-1H-benzo[c]azepin-1-yl)-1H-benzo[d]imidazole-4-carboxamide; 2-(1-methylisoindolin-1-yl)-1H-benzo[d]imidazole-4-carboxamide; 2-(2,3,4,5-tetrahydro-1H-benzo[c]azepin-1-yl)-1H-benzo[d]imidazole-4-carboxamide; hexahydrobenzo[c]azocin-3-yl)-1H-benzo[d]imidazole-4-carboxamide; hexahydrobenzo[d]azocin-2-yl)-1H-benzo[d]imidazole-4-carboxamide; hexahydrobenzo[d]azocin-4-yl)-1H-benzo[d]imidazole-4-carboxamide; 2-(2,3,4,5-tetrahydro-1H-benzo[c]azepin-3-yl)-1H-benzo[d]imidazole-4-carboxamide; 2-(2,3,4,5-tetrahydro-1H-benzo[d]azepin-2-yl)-1H-benzo[d]imidazole-4-carboxamide; 2-(2-methyl-1,2,3,4,5,6-hexahydrobenzo[d]azocin-2-yl)-1H-benzo[d]imidazole-4-carboxamide; 2-(2-methyl-2,3,4,5-tetrahydro-1H-benzo[d]azepin-2-yl)-1H-benzo[d]imidazole-4-carboxamide; 2-(3-ethyl-1,2,3,4-tetrahydroisoquinolin-3-yl)-1H-benzo[d]imidazole-4-carboxamide; 2-(3-ethyl-2,3,4,5-tetrahydro-1H-benzo[c]azepin-3-yl)-1H-benzo[d]imidazole-4-carboxamide; 2-(3-methyl-1,2,3,4,5,6-hexahydrobenzo[c]azocin-3-yl)-1H-benzo[d]imidazole-4-carboxamide; 2-(3-methyl-2,3,4,5-tetrahydro-1H-benzo[c]azepin-3-yl)-1H-benzo[d]imidazole-4-carboxamide; 2-(4-ethyl-1,2,3,4,5,6-hexahydrobenzo[d]azocin-4-yl)-1H-benzo[d]imidazole-4-carboxamide; 2-(4-methyl-1,2,3,4,5,6-hexahydrobenzo[d]azocin-4-yl)-1H-benzo[d]imidazole-4-carboxamide; 6-fluoro-2-(1,2,3,4,5,6-hexahydrobenzo[d]azocin-4-yl)-1H-benzo[d]imidazole-4-carboxamide; 6-fluoro-2-(1,2,3,4-tetrahydroisoquinolin-3-yl)-1H-benzo[d]imidazole-4-carboxamide; and 6-fluoro-2-(2,3,4,5-tetrahydro-1H-benzo[c]azepin-3-yl)-1H-benzo[d]imidazole-4-carboxamide. These are merely representative of compounds embodied herein and useful for the purposes described herein.

2) Biological Activity:

1. In vitro activity of the compounds embodied herein can be assayed by the following methods.

Poly (ADP-Ribose) Polymerase-1 (PARP-1) In Vitro Enzyme Assay: Compounds can be screened for inhibitory activity against human PARP-1 in vitro using the Universal Colorimetric PARP Assay Kit (Trevigen Inc., Gaithersburg, Md.) as directed by the supplier. Compounds can be assayed in duplicate in 0.5% DMSO final concentration, negative control is no enzyme, while positive control is DMSO vehicle alone. $IC_{50}$ determinations can be made using Microsoft Excel. For all cell assays, compounds can be added to cells in 5% DMSO/PBS for a final concentration of 0.5% DMSO.

ATP Depletion Assay: To determine effect of PARP-1 inhibitors in preserving cellular ATP levels when challenged with human umbilical cord endothelial cells (HUVEC, Cambrex) can be preincubated with test PARP-1 inhibitors for 10 minutes before the addition of 250 uM $H_2O_2$. Cells can then be incubated for an additional 1 hour and relative cellular ATP levels measured with CellTiter-Glo Luminescent Cell Viability Assay (Promega Corp.).

Mitochondrial Respiration Assay: To determine efficacy of PARP-1 inhibitors in preserving mitochondrial respiration when again challenged with $H_2O_2$, HUVEC cells can again be preincubated ten minutes with test compounds before the addition of 250 uM $H_2O_2$. One hour later 3-(4,5-dimethylthiazol-2-yl)-2,5,-diphenyltetrazolium bromide (MTT) can be added and incubation continued for an additional 2 hours. At this time the extent of mitochondrial-dependent reduction of MTT to formazan within the cells can be quantitated by the measurement at OD at 570 nm.

Poly-ADP Ribosylation Assay: To measure the efficacy of compounds for directly inhibiting the PARP dependent ribosylation of target proteins (autoADP-ribosylation being the major product), test compounds can be added to the HUVEC cells 10 minutes before the addition of 500 uM $H_2O_2$ to induce PARP-1 activity. Cells can then be incubated for 10 minutes, washed with PBS and lysed. Protein equivalents of resultant cell lysates are then analyzed by SDS-PAGE, blotted to PVDF membranes and probed with the rabbit anti-Poly-(ADP ribose) (PAR) antibody (Calbiochem). Specific antibody reactivity can be detected with the addition of goat-anti rabbit HRP conjugated second antibody (Cell Signaling), ECL substrate and developed on film.

HUVEC Cell Assays are conducted as described by C. Szabo, S Cuzzaocrea, B Zingarelli, M O'Connor, and A L Salzman. Endothelial dysfunction in a rat model of endotoxic shock; importance of the activation of poly (ADP-ribose) synthetase by peroxynitrite. J. Clin. Invest. 1997, 100(3); 723-735.

Potentiation of anticancer compound activity in vitro. To determine the cytotoxicity of a compound of the invention towards a tumor cell line or, in the case of the ability to potentiate the anticancer activity of a chemotherapeutic compound, temozolomide can be used. The human non-small cell lung cancer cell line A549 cells are plated at $10^4$ cells/well of 96 well tissue culture plate. If a combination is being tested, twenty-four hours later temozolomide (250 and 50 micromolar) can be added to the cells alone or plus the addition of 10 micromolar test compound. Cells are then incubated for an additional 72 hours and mitochondrial respiration as a measure of cell viability is assayed by MTT. Inventive compound is able to increase the anti-proliferative effect of 250 and 50 micromolar temozolomide.

Compound Cell Toxicity Assay: This test can be conducted to determine cell toxicity of compounds by prolonged incubation with HUVEC cells. HUVEC cells can be treated with test compounds (again 0.5% DMSO vehicle final concentration) for 46 hours. At this time the mitochondrial respiratory dye MTT is added and incubated for 2 hours. The reduction of MTT to formazan is then quantitated at OD570, and this measure is used as general gauge of cell viability; comprising cell growth and proliferation, apoptosis and necrosis.

The extent of inhibition of PARP activity ($IC_{50}$, micromolar) in the following compounds is provided using the following letter codes: A, >2 micromolar; B, 2.0-0.5 micromolar; and C, <0.5 micromolar. A: benzyl 2-(4-carbamoyl-1H-benzo[d]imidazol-2-yl)indoline-1-carboxylate; benzyl 1-(4-carbamoyl-1H-benzo[d]imidazol-2-yl)-3,4-dihydroisoquinoline-2(1H)-carboxylate; benzyl 1-(4-carbamoyl-1H-benzo[d]imidazol-2-yl)isoindoline-2-carboxylate; tert-butyl 2-(4-carbamoyl-1H-benzo[d]imidazol-2-yl)-3,4-dihydroquinoline-1(2H)-carboxylate; benzyl 3-(4-carbamoyl-1H-benzo[d]imidazol-2-yl)-3-methyl-3,4-dihydroisoquinoline-2(1H)-carboxylate; tert-butyl 7-((tert-butoxycarbonyl)amino)-3-(4-carbamoyl-1H-benzo[d]imidazol-2-yl)-3,4-dihydroisoquinoline-2(1H)-carboxylate; tert-butyl 7-amino-3-(4-carbamoyl-1H-benzo[d]imidazol-2-yl)-3,4-dihydroisoquinoline-2(1H)-carboxylate; and tert-butyl (3-(4-carbamoyl-1H-benzo[d]imidazol-2-yl)-1,2,3,4-tetrahydroisoquinolin-7-yl)carbamate. B: benzyl 3-(4-carbamoyl-1H-benzo[d]imidazol-2-yl)-3,4-dihydroisoquinoline-2(1H)-carboxylate. C: 2-(1,2,3,4-tetrahydroisoquinolin-3-yl)-1H-benzo[d]imidazole-4-carboxamide; 2-(indolin-2-yl)-1H-benzo[d]imidazole-4-carboxamide; 2-(1,2,3,4-tetrahydroisoquinolin-1-yl)-1H-benzo[d]imidazole-4-carboxamide; 2-(isoindolin-1-yl)-1H-benzo[d]imidazole-4-carboxamide; 2-(1,2,3,4-tetrahydroquinolin-2-yl)-1H-benzo[d]imidazole-4-carboxamide; 2-(3-methyl-1,2,3,4-tetrahydroisoquinolin-3-yl)-1H-benzo[d]imidazole-4-carboxamide; and 2-(7-amino-1,2,3,4-tetrahydroisoquinolin-3-yl)-1H-benzo[d]imidazole-4-carboxamide.

2. In Vivo.

Inhibition of Poly (ADP-ribosylation) as determined by brain immunohistochemistry. In the rat MCAO model, test compound can be administered i.v. (5 mg/kg body weight) in a proof of concept study for evidence of brain bioavailability. One hour after onset of occlusion, animals can be sacrificed, perfused, and the brains removed. Frozen section can be cut and processed by immunohistochemistry for levels of poly (ADP-ribose) in the immediate zone adjacent to the infarct.

Stroke model: inhibition of infarct development when administered at time of occlusion and 4 hours post occlusion. Compound can be administered, 5 mg/kg i.v., at time of occlusion, 20 mg/kg i.p immediately after confirmation of occlusion, and at 20 hrs, with sacrifice at 24 hrs. For delayed treatment in the MCAO model, animals can be dosed intraperitoneally at 4 hours, and 20 hours post-occlusion and sacrificed at 72 hrs. All animals can be anesthetized, perfused and processed for TTC staining.

Myocardial infarction model. The effect of a compound of the invention can be examined in a rat model of in vivo myocardial ischemia and reperfusion. Regional myocardial ischemia can be initiated by ligating the left anterior descending coronary artery for 45 min (LAD occlusion). After 45 min ischemia, the occlusion can be released. In one study, the test compound can be administered (5 mg/kg-body weight, iv) before ischemia. In another study, test compound administration (5 mg/kg-body weight, iv) can be delayed after ischemia (45 min of LAD occlusion). Following 2 hours reperfusion, animals (n=6/group) can be sacrificed and infarct size estimated as a percentage of the area at risk (Evans blue+TTC). Then the above sections can be formalin preserved and paraffin embedded sections evaluated for myocardial apoptosis using the fluorescent Dead End Fluorometric TUNEL System (Promega Corp, Madison, Wis.) according to manufacturer's instructions. Quantitative analysis can be performed using Bioquant Image Analysis Soft ware program (Bioquant, Nashville, Tenn.).

What is claimed is:
1. A compound of Formula (I):

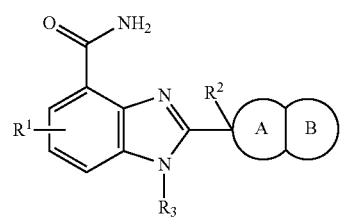

wherein $R^1$ is one or more H, hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkynyl, optionally substituted aliphatic, alicyclic, heteroaliphatic, or heterocyclic;

$R^2$ is H, optionally substituted alkyl or cycloalkyl;

$R^3$ is H, $COR^4$, $CONR^4R^5$, $COOR^4$, $SO_2R^4$, optionally substituted alkyl, alkenyl, alkynyl, cyclolalkyl, heterocycloalkyl, aryl or heteroaryl;

$R^4$ and $R^5$ are independently selected from the group consisting of H, OH, $NH_2$, alkyl, alkenyl, alkynyl, cycloalkyl, heterocycloalkyl, aryl, or heteroaryl;

A and B joined together form a bicyclic ring wherein:

A is nonaromatic 4, 5, 6, 7 or 8-membered ring that contains 1 or 2 nitrogen atoms and optionally one sulfur or oxygen atom, where in the nonaromatic ring is optionally substituted with 1, 2 or 3 substituents selected from the group consisting of hydroxy, halogen, cyano, $OR^4$, nitro, $NH_2$, $NR^4R^5$, $NR^4COR^5$, $NR^4SO_2R^4$, $CONR^4R^5$, $COOR^4$, $SO_2R^4$, alkyl, alkenyl, alkynyl, alkoxyalkyl, alkoxycarbonylalkyl, cycloalkyl, cycloalkylalkyl, haloalkyl, heterocycle, heterocycloalkyl, aryl, arylalkyl, heteroaryl, heteroarylalkyl and oxo; and B is aryl or heteroaryl that is optionally substituted with 1, 2 or 3 substituents selected from the group consisting of hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkyl, alkenyl, alkynyl, alkoxyalkyl, alkoxycarbonylalkyl, cycloalkyl, cycloalkylalkyl, haloalkyl, heterocycle, heterocycloalkyl, aryl, arylalkyl, heteroaryl, and heteroarylalkyl.

2. The compound of claim 1 wherein $R^1$ is H, Cl or F.

3. The compound of claim 1 wherein $R^2$ is H, methyl or ethyl.

4. The compound of claim 1 wherein $R^3$ is H.

5. The compound of claim 1 wherein $R^4$ and $R^5$ are independently H, methyl or ethyl.

6. The compound of claim 1 wherein A and B taken together is indolin-2-yl, isoindolin-1-yl, 1,2,3,4-tetrahydroisoquinolin-1-yl, 1,2,3,4-tetrahydroquinolin-2-yl, 1,2,3,4-tetrahydroisoquinolin-3-yl, 2,3,4,5-tetrahydro-1H-benzo[b]azepin-2-yl, 2,3,4,5-tetrahydro-1H-benzo[c]azepin-3-yl, 2,3,4,5-tetrahydro-1H-benzo[d]azepin-2-yl, 2,3,4,5-tetrahydro-1H-benzo[c]azepin-1-yl, 1,2,3,4,5,6-hexahydrobenzo[b]azocin-2-yl, 1,2,3,4,5,6 hexahydrobenzo[c]azocin-3-yl, 1,2,3,4,5,6-hexahydrobenzo[d]azocin-2-yl, 1,2,3,4,5,6-hexahydrobenzo[c]azocin-1-yl or 1,2,3,4,5,6-hexahydrobenzo[d]azocin-4-yl.

7. The compound of claim 1 selected from benzyl 2-(4-carbamoyl-1H-benzo[d]imidazol-2-yl)indoline-1-carboxylate; 2-(indolin-2-yl)-1H-benzo[d]imidazole-4-carboxamide; tert-butyl 2-(4-carbamoyl-1H-benzo[d]imidazol-2-yl)-3,4-dihydroquinoline-1(2H)-carboxylate; 2-(1,2,3,4-tetrahydroquinolin-2-yl)-1H-benzo[d]imidazole-4-carboxamide; benzyl 1-(4-carbamoyl-1H-benzo[d]imidazol-2-yl)isoindoline-2-carboxylate; 2-(isoindolin-1-yl)-1H-benzo[d]imidazole-4-carboxamide; benzyl 1-(4-carbamoyl-1H-benzo[d]imidazol-2-yl)-3,4-dihydroisoquinoline-2(1H)-carboxylate; 2-(1,2,3,4-tetrahydroisoquinolin-1-yl)-1H-benzo[d]imidazole-4-carboxamide; benzyl 3-(4-carbamoyl-1H-benzo[d]imidazol-2-yl)-3,4-dihydroisoquinoline-2(1H)-carboxylate; 2-(1,2,3,4-tetrahydroisoquinolin-3-yl)-1H-benzo[d]imidazole-4-carboxamide; benzyl 3-(4-carbamoyl-1H-benzo[d]imidazol-2-yl)-3-methyl-3,4-dihydroisoquinoline-2(1H)-carboxylate; 2-(3-methyl-1,2,3,4-tetrahydroisoquinolin-3-yl)-1H-benzo[d]imidazole-4-carboxamide; tert-butyl 7-((tert-butoxycarbonyl)amino)-3-(4-carbamoyl-1H-benzo[d]imidazol-2-yl)-3,4-dihydroisoquinoline-2(1H)-carboxylate; tert-butyl 7-amino-3-(4-carbamoyl-1H-benzo[d]imidazol-2-yl)-3,4-dihydroisoquinoline-2(1H)-carboxylate; tert-butyl (3-(4-carbamoyl-1H-benzo[d]imidazol-2-yl)-1,2,3,4-tetrahydroisoquinolin-7-yl)carbamate and 2-(7-amino-1,2,3,4-tetrahydroisoquinolin-3-yl)-1H-benzo[d]imidazole-4-carboxamide.

8. The compound of Formula (IV) below:

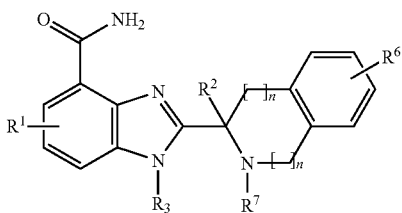

IV wherein $R^1$ and $R^6$ are one or more H, hydroxy, halogen, cyano, $OR^4$, nitro, $NH_2$, $NR^4R^5$, $NR^4COR^5$, $NR^4SO_2R^5$, $CONR^4R^5$, $COOR^4$, $SO_2R^4$, alkynyl, optionally substituted aliphatic, alicyclic, heteroaliphatic or heterocyclic;

$R^2$ is H, optionally substituted alkyl or cycloalkyl;

$R^3$ and $R^7$ are independently selected from the group consisting of H, $COR^4$, $CONR^4R^5$, $COOR^4$, $SO_2R^4$, optionally substituted alkyl, alkenyl, alkynyl, cyclolalkyl, heterocycloalkyl, aryl and heteroaryl;

$R^4$ and $R^5$ are independently selected from the group consisting of H, OH, NH2, alkyl, alkenyl, alkynyl, cycloalkyl, heterocycloalkyl, aryl, and heteroaryl; and n=0, 1, 2 or 3.

9. The compound of claim 8 wherein $R^1$ is H, Cl or F.

10. The compound of claim 8 wherein $R^2$ is H, methyl or ethyl.

11. The compound of claim 8 wherein $R^3$ is H.

12. The compound of claim 8 wherein $R^4$ and $R^5$ are independently H, methyl or ethyl.

13. The compound of claim 8 wherein $R^6$ is H or F.

14. The compound of claim 8 wherein $R^7$ is H, methyl, ethyl, propyl, isopropyl, t-butyl, cyclopropyl, cyclobutyl, cyclopentyl, 2-fluorobenzyl or phenylethyl.

15. The compound of claim 8 selected from benzyl 3-(4-carbamoyl-1H-benzo[d]imidazol-2-yl)-3,4-dihydroisoquinoline-2(1H)-carboxylate; 2-(1,2,3,4-tetrahydroisoquinolin-3-yl)-1H-benzo[d]imidazole-4-carboxamide; benzyl 3-(4-carbamoyl-1H-benzo[d]imidazol-2-yl)-3-methyl-3,4-dihydroisoquinoline-2(1H)-carboxylate; 2-(3-methyl-1,2,3,4-tetrahydroisoquinolin-3-yl)-1H-benzo[d]imidazole-4-carboxamide; tert-butyl 7-((tert-butoxycarbonyl)amino)-3-(4-carbamoyl-1H-benzo[d]imidazol-2-yl)-3,4-dihydroisoquinoline-2(1H)-carboxylate; tert-butyl 7-amino-3-(4-carbamoyl-1H-benzo[d]imidazol-2-yl)-3,4-dihydroisoquinoline-2(1H)-carboxylate; tert-butyl (3-(4-carbamoyl-1H-benzo[d]imidazol-2-yl)-1,2,3,4-tetrahydroisoquinolin-7-yl)carbamate and 2-(7-amino-1,2,3,4-tetrahydroisoquinolin-3-yl)-1H-benzo[d]imidazole-4-carboxamide.

16. A pharmaceutical composition comprising a compound of claim 1 and a pharmaceutically acceptable carrier, excipient or diluent.

17. A method for inhibiting PARP activity in a patient or a biological sample, which method comprises administering to the patient or exposing the biological sample to an effective amount of a compound of claim 1 or a pharmaceutical composition thereof.

18. A method of treating or lessening the severity of a disease, disorder or condition selected from stroke, myocardial infarction, rheumatoid arthritis and atherosclerosis, which method comprises administering to a patient in need thereof an effective amount of a compound claim 1 or a pharmaceutical composition thereof.

19. A pharmaceutical composition comprising a compound of claim 8 and a pharmaceutically acceptable carrier, excipient or diluent.

20. A method for inhibiting PARP activity in a patient or a biological sample, which method comprises administering to the patient or exposing the biological sample to an effective amount of a compound of claim 8 or a pharmaceutical composition thereof.

21. A method of treating or lessening the severity of a disease, disorder or condition selected from stroke, myocardial infarction, rheumatoid arthritis and atherosclerosis, which method comprises administering to a patient in need thereof an effective amount of a compound of claim 8 or a pharmaceutical composition thereof.

* * * * *